(12) United States Patent
Utsunomiya et al.

(10) Patent No.: US 10,487,032 B2
(45) Date of Patent: Nov. 26, 2019

(54) PRODUCTION METHOD FOR 1,4-BUTANEDIOL

(71) Applicants: MITSUBISHI CHEMICAL CORPORATION, Chiyoda-ku (JP); GENOMATICA, INC., San Diego, CA (US)

(72) Inventors: Masaru Utsunomiya, Tokyo (JP); Yusuke Izawa, Mie (JP); Norikazu Konishi, Mie (JP); Kota Tanaka, Mie (JP); Shinichiro Matsuzono, Mie (JP); Takayuki Suzuki, Mie (JP); Michael Japs, San Diego, CA (US); Mark Burk, San Diego, CA (US); Warren Clark, Lake Jackson, TX (US)

(73) Assignees: MITSUBISHI CHEMICAL CORPORATION, Chiyoda-ku (JP); GENOMATICA, INC., San Diego, CA (US)

( * ) Notice: Subject to any disclaimer, the term of this patent is extended or adjusted under 35 U.S.C. 154(b) by 598 days.

(21) Appl. No.: 14/560,714

(22) Filed: Dec. 4, 2014

(65) Prior Publication Data

US 2015/0087038 A1 Mar. 26, 2015

Related U.S. Application Data

(63) Continuation of application No. PCT/JP2013/065367, filed on Jun. 3, 2013.

(30) Foreign Application Priority Data

Jun. 5, 2012 (JP) .................................. 2012-128065
Feb. 27, 2013 (JP) .................................. 2013-037301

(51) Int. Cl.
| | | |
|---|---|---|
| C07C 29/84 | (2006.01) | |
| C07C 29/80 | (2006.01) | |
| C12P 7/18 | (2006.01) | |
| B01D 3/14 | (2006.01) | |
| B01D 3/00 | (2006.01) | |

(52) U.S. Cl.
CPC ............. *C07C 29/84* (2013.01); *B01D 3/002* (2013.01); *B01D 3/143* (2013.01); *C07C 29/80* (2013.01); *C12P 7/18* (2013.01)

(58) Field of Classification Search
CPC .................................. C07C 29/84; B01D 3/143
See application file for complete search history.

(56) References Cited

U.S. PATENT DOCUMENTS

| | | | |
|---|---|---|---|
| 4,213,000 A * | 7/1980 | Coates .................. | C07C 29/172 568/861 |
| 5,209,825 A | 5/1993 | Badat et al. | |
| 5,397,439 A | 3/1995 | Kandori et al. | |
| 2005/0069997 A1 | 3/2005 | Adkesson et al. | |
| 2010/0101931 A1* | 4/2010 | Pinkos .................. | C07C 29/80 203/82 |
| 2011/0003355 A1* | 1/2011 | Clark .................... | C07C 29/76 435/158 |
| 2011/0257441 A1 | 10/2011 | Rousseaux et al. | |
| 2014/0116872 A1 | 5/2014 | Izawa et al. | |
| 2014/0187740 A1 | 7/2014 | Izawa et al. | |

FOREIGN PATENT DOCUMENTS

| | | |
|---|---|---|
| CN | 1816629 A | 8/2006 |
| CN | 101284762 A | 10/2008 |
| CN | 102459138 A | 5/2012 |
| JP | 61-197534 A | 9/1986 |
| JP | 6-172235 A | 6/1994 |
| JP | 10-265418 A | 10/1998 |
| JP | 2007-502325 A | 2/2007 |
| JP | 2010-518174 A | 5/2010 |
| JP | 2012-504404 A | 2/2012 |
| WO | WO 2010/141780 A1 | 12/2010 |

OTHER PUBLICATIONS

Varadarajan et al. Biotechnol. Prog., 1999, 15:845-854.*
International Search Report dated Aug. 20, 2013 in PCT/JP2013/065367 (with English language translation).
International Preliminary Report on Patentability and Written Opinion dated Dec. 9, 2014 in PCT/JP2013/065367 (with English language translation).
U.S. Appl. No. 14/150,174, filed Jan. 8, 2014, US2014/0187740 A1, Izawa, et al.
U.S. Appl. No. 14/147,885, filed Jan. 6, 2014, US2014/0116872 A1, Izawa, et al.
Combined Taiwanese Office Action and Search Report dated Oct. 3, 2016 in Patent Application No. 102119878 (with English translation).
Japanese Office Action dated Nov. 29, 2016 in Patent Application No. 2013-117832 (with English translation).
Takaki Muroi, "Catalyst Poison" Industrial Noble Metal Catalysts, May 26, 2003 pp. 36-41 (with English translation).
Office Action dated Aug. 15, 2017 in Taiwanese Patent Application No. 102119878 (with English language translation).

* cited by examiner

*Primary Examiner* — Bin Shen
(74) *Attorney, Agent, or Firm* — Oblon, McClelland, Maier & Neustadt, L.L.P.

(57) ABSTRACT

An object of the present invention is to provide high-quality 1,4BG capable of working out to a raw material of PBT with good color tone, by efficiently removing and refining impurities mixed when producing a biomass-derived 1,4BG on an industrial scale and the present invention relates to a production method of refined 1,4BG, where a crude 1,4BG-containing solution is obtained from refined raw material 1,4BG obtained by removing bacterial cells, salt contents and water from the fermentation culture medium, through a step of removing high-boiling-point components and/or low-boiling-point components by distillation and/or a step of converting an unsaturated compound to a hydride and the target product is obtained as a side stream in a further distillation step.

19 Claims, 3 Drawing Sheets

PRODUCTION METHOD FOR 1,4-BUTANEDIOL

TECHNICAL FIELD

The present invention relates to a production method for 1,4-butanediol. More specifically, the present invention relates to a method for producing high-purity refined 1,4-butanediol by refining crude 1,4-butanediol obtained from biomass resources.

BACKGROUND ART 1,4-Butanediol (hereinafter, sometimes simply referred to as "1,4BG") is a very useful substance used as a raw material of various solvents or derivatives.

Conventionally, a variety of methods for industrially producing 1,4BG by using petroleum or other fossil fuels as a raw material are known. For example, there are a method where diacetoxybutene is obtained as an intermediate by an acetoxylation reaction using acetic acid and oxygen and using butadiene as a raw material and the diacetoxybutene is hydrogenated and hydrolyzed to produce 1,4BG; a method where maleic acid, succinic acid, maleic anhydride and/or fumaric acid are used as raw materials and these materials are hydrogenated to obtain a 1,4BG-containing crude hydrogenation product; and a method where butynediol obtained using acetylene as a raw material by contacting it with an aqueous formaldehyde solution is hydrogenated to produce 1,4BG.

Recently, a method for producing a biomass-derived 1,4BG by using a biomass resource as a raw material has also been developed, in addition to the conventional method of producing 1,4BG by using petroleum or other fossil fuels as a raw material. For example, there are a method where succinic acid obtained by the fermentation of a sugar is hydrogenated to obtain 1,4BG (Patent Document 1), and a method where 1,4BG is directly obtained by fermenting a biomass resource such as sugar (Patent Document 2).

When a product comparable to a petrochemical product produced from a fossil fuel such as petroleum is produced from a biomass resource, a refining process on an industrial scale (large-scale process) is necessary for stably maintaining the production volume or quality. For example, in the case where the biomass resource used as a raw material is a sugar or the like, the target product is obtained by the fermentation thereof with bacteria, but for maintaining the quality equivalent to that of a product obtained by the conventional production process using a fossil fuel such as petroleum, a refinement technique capable of highly removing impurities contained in the raw material or various byproducts generated in the course of fermentation is required.

As an example of such a refinement technique, a refinement method regarding biomass-derived 1,3-propanediol is described in Patent Document 3.

Also, as a method for refining biomass-derived 1,4BG, a general refinement method is described in Patent Document 4.

BACKGROUND ART DOCUMENT

Patent Document

Patent Document 1: JP-A-2009-077719 (the term "JP-A" as used herein means an "unexamined published Japanese patent application")

Patent Document 2: JP-T-2010-521182 (the term "JP-T" as used herein means a published Japanese translation of a PCT patent application)

Patent Document 3: JP-T-2007-502325

Patent Document 4: U.S. Patent Application Publication 2011/0003355

SUMMARY OF INVENTION

Problem that Invention is to Solve

However, Patent Document 4 lacks, for example, a specific reference to detailed refinement conditions or substances responsible for deterioration of quality and is silent on the method for removing such substances, and the method can be hardly applied to a large-scale process in industry.

Also, at the time of production of polybutylene terephthalate (hereinafter, sometimes simply referred to as "PBT") that is one of principal uses of 1,4BG, when biomass-derived 1,4BG is used as a raw material for the PBT production, impurities derived from the raw material or various impurities generated in the course of fermenting the biomass resource such as sugar may be mixed, as a result, the color tone may be deteriorated, compared with PBT starting from the conventional 1,4BG derived from a fossil fuel such as petroleum.

Under these circumstances, the present invention has been made, and an object of the present invention is to provide a method for producing a high-quality biomass-derived 1,4BG capable of working out to a raw material of PBT with good color tone, where various impurities mixed when producing biomass-derived 1,4BG on an industrial scale can be efficiently removed and refined.

Means for Solving Problem

The present inventors have made intensive studies to attain the above-described object. As a result, it has been found that in a distillation column used at the refinement step when producing biomass-derived 1,4BG on an industrial scale, fouling proceeds due to precipitation of a solid matter and deterioration in the quality of 1,4BG proceeds due to production of tetrahydrofuran (hereinafter, sometimes simply referred to as "THF") and water; the quality deterioration above can be overcome by employing a refinement process that passes through a specific refinement step; and when producing PBT by using biomass-derived 1,4BG, the concentration of a cyclic carbonyl compound having a carbon atom number of 5 or 6 contained in the raw material 1,4BG is correlated with coloring of PBT and by removing the cyclic carbonyl compound in the refinement step of biomass-derived 1,4BG and controlling the concentration of the compound to fall in a specific range, the color tone of PBT obtained can be improved. The present invention has been accomplished based on these findings.

That is, the gist of the present invention resides in the following <1> to <15>.

<1> A method for producing 1,4-butanediol, comprising biologically producing 1,4-butanediol in a culture medium for fermentation of an organism capable of producing 1,4-butanediol, at least partially removing each of a bacterial cell, a salt content and water from said fermentation culture medium to obtain a refined raw material 1,4-butanediol-containing solution, obtaining therefrom a crude 1,4-butanediol-containing solution through any one or more steps of the following steps (a) to (c), refining said crude 1,4- butanediol-containing solution through the following step (d) to obtain refined 1,4-butanediol:

Step (a):
   a step of distilling said refined raw material 1,4-butanediol-containing solution in a distillation column to remove components which are contained in said refined raw material 1,4-butanediol-containing solution and higher in the boiling point than 1,4-butanediol;

Step (b):
   a step of distilling said refined raw material 1,4-butanediol-containing solution in a distillation column to remove components which are contained in said refined raw material 1,4-butanediol-containing solution and lighter in the boiling point than 1,4-butanediol;

Step (c):
   a hydrogenation step of at least partially converting unsaturated compounds contained in said refined raw material 1,4-butanediol-containing solution into a hydride; and Step (d):
   a step of distilling said crude 1,4-butanediol-containing solution in a distillation column and withdrawing refined 1,4-butanediol from a side stream.

<2> The method for producing 1,4-butanediol as described in the above <1>, wherein the concentration of a cyclic carbonyl compound having a carbon atom number of 5 or 6 in the refined 1,4-butanediol obtained in said step (d) is 12 ppm by mass or less.

<3> The method for producing 1,4-butanediol as described in the above <1> or <2>, which is a method for producing 1,4-butanediol through at least the step (a) out of said steps (a) to (c) and further passes through the following step (e):

Step (e):
   a step of distilling components higher in the boiling point than 1,4-butanediol, which are separated in said step (a), in a distillation column and thereby separating and recovering 1,4-butanediol.

<4> The method for producing 1,4-butanediol as described in any one of the above <1> to <3>, which is a method for producing 1,4-butanediol through at least the step (c) out of said steps (a) to (c), wherein the refined raw material 1,4-butanediol-containing solution after passing through the following step (f) is introduced into said step (c):

Step (f):
   a step of brining said refined raw material 1,4-butanediol-containing solution into contact with a base.

<5> The method for producing 1,4-butanediol as described in any one of the above <1> to <4>, wherein the water concentration in the refined raw material 1,4-butanediol-containing solution immediately before passing through any one step of said steps (a) to (c) or through the step (f) is from 0.01 to 20 mass % and the pH thereof is 5 or more.

<6> The method for producing 1,4-butanediol as described in any one of the above <1> to <5>, wherein in the hydrogenation step of said step (c), hydrogenation is performed using a solid catalyst having a nickel-containing metal supported on at least either kieselguhr or silica.

<7> The method for producing 1,4-butanediol as described in any one of the above <4> to <6>, wherein the base in said step (f) is a solid base.

<8> The method for producing 1,4-butanediol as described in any one of the above <1> to <7>, wherein the components lighter in the boiling point than 1,4-butanediol in said step (b) contain 1-acetoxy-4-hydroxybutane and the 1-acetoxy-4-hydroxybutane concentration in the crude 1,4-butanediol-containing solution after the removal of said components lighter in the boiling point than 1,4-butanediol is from 0.1 to 50 ppm by mass.

<9> The method for producing 1,4-butanediol as described in any one of the above <1> to <8>, wherein the bottom temperature of the distillation column in said step (b) is from 120 to 200° C.

<10> The method for producing 1,4-butanediol as described in any one of the above <1> to <9>, wherein the bottom temperature of the distillation column in said step (a) is from 150 to 200° C.

<11> The method for producing 1,4-butanediol as described in any one of the above <1> to <10>, wherein the components higher in the boiling point than 1,4-butanediol in said step (a) contain 2-pyrrolidone and the 2-pyrrolidone concentration in the crude 1,4-butanediol-containing solution after the removal of said components higher in the boiling point than 1,4-butanediol is 20 ppm by mass or less.

<12> The method for producing 1,4-butanediol as described in any one of the above <1> to <11>, wherein a heating source of the distillation column in said step (a) contacts substantially only with the bottom liquid but involves no contact with a gas-phase part.

<13> The method for producing 1,4-butanediol as described in any one of the above <1> to <12>, wherein the gamma-butyrolactone concentration in the overhead distillate of the distillation column in said step (d) is higher than the gamma-butyrolactone concentration in the refined 1,4-butanediol withdrawn from a side stream.

<14> The method for producing 1,4-butanediol as described in any one of the above <1> to <13>, comprising a step of controlling the carbonyl value in the refined raw material 1,4-butanediol-containing solution immediately before passing through any one step of said steps (a) to (c) or through the step (f), to be 2.5 mgKOH/g or less.

<15> The method for producing 1,4-butanediol as described in any one of the above <1> to <14>, wherein in at least one step of said steps (b) to (d), the carbonyl value in said refined raw material 1,4-butanediol-containing solution is reduced.

Advantageous Effects of Invention

According to the present invention, high-quality 1,4BG capable of working out to a raw material of PBT with good color tone can be produced, by efficiently removing and refining impurities mixed when producing a biomass-derived 1,4BG on an industrial scale.

MODE FOR CARRYING OUT INVENTION

Figure 1:
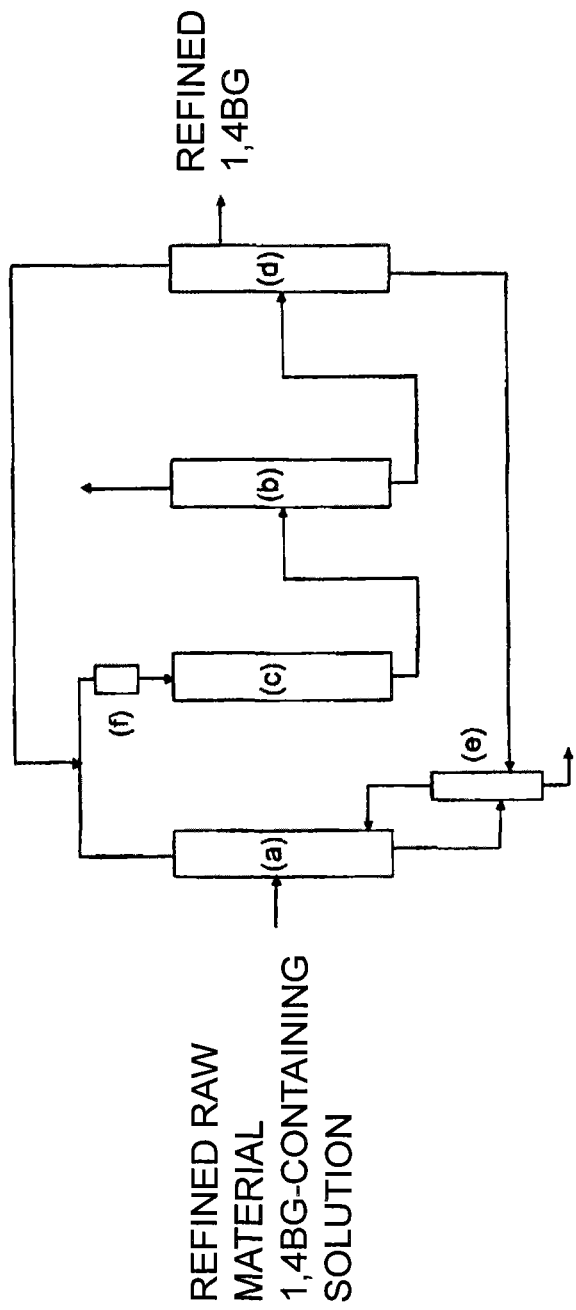
FIG. 1 is a systematic diagram of steps (a) to (f) illustrating a preferred embodiment of the present invention.

The present invention is described in detail below, but the respective constituent requirements described below are a representative example of the embodiment of the present invention, and the present invention is not limited to them.

Incidentally, a numerical range expressed by using the expression "(numerical value) to (numerical value)" in the description of the present invention means a range which includes the numerical values before and after "to" as a lower limit and an upper limit, respectively. In addition, a lower limit or an upper limit in the description of the present invention means a range which includes a numerical value of the lower limit or the upper limit.

Incidentally, in the description of the present invention, the expression "wt %", "ppm by weight" and "weight ratio" have the same meanings as "mass %", "ppm by mass" and "mass ratio", respectively. Also, when simply referred to as "ppm", this indicates "ppm by weight".

The purification process in the production method for 1,4-BG of the present invention is preferably applied to a biomass-derived 1,4BG-containing composition.

The biomass material includes a material in which light energy of the sun is converted into a form of starch, cellulose or the like by photonic synthesis of a plant and stored, the body of an animal which grows by eating plants, a product obtained by processing a plant body or an animal body and the like.

Specifically, wood, paddy straw, rice bran, old rice, corn, sugar cane, cassava, sago palm, soy pulp, corncobs, tapioca refuse, bagasse, vegetable oil refuse, potatoes, buckwheat, soybeans, fat, old papers, papermaking residues, fishery product residues, excreta from domestic animals, sewage sludge, food wastes and the like are mentioned. Among them, plant materials such as wood, paddy straw, old rice, corn, sugar cane, cassava, sago palm, soy pulp, corncobs, tapioca refuse, bagasse, vegetable oil refuse, potatoes, buckwheat, soybeans, fat, old papers and papermaking residues are preferable. More preferable materials are wood, paddy straw, old rice, corn, sugar cane, cassava, sago palm, potatoes, fat, old papers, papermaking residues and the like and most preferable materials are corn, sugar cane, cassava and sago palm.

The biomass materials generally contain nitrogen atom, many alkali metals and alkaline earth metals such as Na, K, Mg and Ca.

These biomass materials are induced to carbon sources through a known pretreatment/saccharification step and the like, such as chemical treatment using an acid, an alkali or the like, biological treatment using a microorganism and physical treatment, although the method is not particularly limited. The step often includes a step for reducing the size through pretreatment for chipping, shaving or mashing the biomass material, and if necessary, further includes a pulverization step using a grinder or a mill.

The biomass material which has been thus reduced in size is generally induced to a carbon source through a further pretreatment/saccharification step. Examples of the specific method are: chemical methods such as acid treatment using a strong acid such as sulfuric acid, nitric acid, hydrochloric acid or phosphoric acid, alkali treatment, ammonia freezing steam blasting method, extraction with a solvent, supercritical fluid treatment and treatment with an oxidizing agent; physical methods such as pulverization, steam blasting method, microwave treatment and irradiation with electron beams; and biological treatment such as hydrolysis by treatment with a microorganism or an enzyme.

In general, as the carbon source induced from the above biomass materials, following fermentative carbohydrates and the like are used: hexoses such as glucose, mannose, galactose, fructose, sorbose and tagatose; pentoses such as arabinose, xylose, ribose, xylulose and ribulose; di- and polysaccharides such as pentosan, saccharose, starch and cellulose; fat such as butyric acid, caproic acid, caprylic acid, capric acid, lauric acid, myristic acid, palmitic acid, palmitoleic acid, stearic acid, oleic acid, linoleic acid, linolenic acid, monocutinic acid, arachidic acid, eicosenoic acid, arachidonic acid, behenic acid, erucic acid, docosapentaenoic acid, docosahexaenoic acid, lignoceric acid and selacholeic acid; and polyalcohols such as glycerin, mannitol, xylitol and ribitol. Among them, hexoses, pentoses or disaccharides such as glucose, fructose, xylose or saccharose is preferable and glucose is particularly preferable. Cellulose, which is the main component of papers, is also preferable as the plant-derived carbon source in a broader sense.

In the method of producing 1,4BG directly from a carbon source such as glucose by a fermentation process, transgenic E. coli, a coryneform bacterium, a yeast, etc. can be used. For example, 1,4BG can be biologically produced in a culture medium for organism fermentation by the method described in JP-T-2010-521182.

In addition, a composition containing 1,4BG that is thus biologically produced in a culture medium for fermentation of an organism capable of producing 1,4BG can be obtained, for example, by entirely or at least partially separating and removing bacterial cells and salt contents by any one separation means or two or more separation means of filtration, centrifugal separation and an ion-exchange resin based on U.S. Patent Application Publication No. 2011/0003355, and furthermore, a refined raw material 1,4BG-containing solution can be obtained from the 1,4BG-containing composition above by at least partially removing water in the composition.

In the present invention, the "1,4BG-containing composition" indicates a composition after removing bacterial cells and salt contents from the fermentation culture medium in which 1,4BG is produced, and the residue after removing water from the 1,4BG-containing composition above is referred to as "refined raw material 1,4BG-containing solution".

The method for removing water contained in the 1,4BG-containing composition after separating and removing bacterial cells and salt contents from the fermentation culture medium is not particularly limited, but these are preferably removed by continuous or batch distillation. As the distillation column used for the distillation/removal of water, a distillation column having from 2 to 100 plates as the theoretical plate is preferably used, and the number of theoretical plates is more preferably from 5 to 50.

The reflux ratio is arbitrary but is preferably from 0.01 to 100. The reflux ratio is more preferably from 0.1 to 50, still more preferably from 0.2 to 20.

The reboiler as the heating region of a distillation column is not particularly limited but is preferably a forced circulation reboiler or a falling film reboiler. In particular, the residence time in the contact region with a heating source at the bottom is preferably shorter so as to avoid fouling, and a structure where the heating source is not put into contact with a gas-phase part or a structure where the amount of contact is minimized, is preferred.

The top pressure of the distillation column is, in terms of absolute pressure, preferably from 1 to 200 kPa, more preferably from 2 to 100 kPa, still more preferably from 5 to 50 kPa. As the top pressure is lower, the temperature in the column can be reduced, and production of new impurities from biomass-derived components such as amino acid and sugar can be thereby prevented, but if the top pressure is too low, cooling becomes inefficient. Also, as the top pressure is higher, the volume of the column itself can be reduced, but if the top pressure is too high, the bottom temperature rises and impurities are likely to be produced.

The temperature in the distillation column is determined by the composition and pressure, but the temperature in the bottom where the temperature becomes highest is preferably from 120 to 200° C., more preferably from 140 to 190° C., still more preferably from 150 to 180° C. By setting the bottom temperature of the distillation column to be higher than the lower limit above, the top temperature can also be high and the cooling cost can be kept low. Also, by setting the bottom temperature to be lower than the upper limit above, impurities due to a side reaction of biomass-derived components can be decreased.

The top temperature is preferably from 40 to 100° C., more preferably from 40 to 80° C., still more preferably from 40 to 60° C. By setting the top temperature to be not less than the lower limit above, the cooling cost can be kept low, and by setting the top temperature to be not more than the upper limit above, a side reaction in the column can be suppressed.

The preferable overhead distribution ratio (=(flow rate of overhead distillate/flow rate of feed)×100) in the distillation column varies depending on the water concentration in the 1,4BG-containing composition but is preferably from 2 to 40%, more preferably from 5 to 30%, still more preferably from 8 to 25%. If the overhead distribution ratio is too high, the loss of 1,4BG is increased, whereas if the overhead distribution ratio is too small, a fairly large amount of water and light-boiling acid are carried over into the 1,4BG-containing solution fed to the next step, that is, the refined raw material 1,4BG-containing solution.

In this distillation column, the pH in the bottom is preferably controlled to be from 4 to 9, more preferably from 5 to 8. If the pH is too low, by-production of THF is increased in the distillation column and the operation becomes difficult. If the pH is too high, a side reaction such as occurrence of high boiling is promoted.

The bottom product obtained from the distillation column of removing water, that is, the refined raw material 1,4BG-containing solution, is fed to the next refinement step. A distillate containing water and a large number of light-boiling-point components may be discarded as it is but may be used for washing, etc. of other steps.

The refined raw material 1,4BG-containing solution obtained by removing water from the 1,4BG-containing composition by such a distillation operation is withdrawn from the bottom of the distillation column above. This refined raw material 1,4BG-containing solution contains 1,4BG and components higher or lighter in the boiling point than 1,4BG.

The components except for 1,4BG, contained in the refined raw material 1,4BG-containing solution, are gamma-butyrolactone, 1-acetoxy-4-hydroxybutane, tetrahydrofuran, acetic acid, butanol, butylaldehyde, butyric acid, 1,3-butanediol, 2,3-butanediol, 2-hydroxytetrahydrofuran, 2-(4-hydroxybutyloxyl)tetrahydrofuran, water, nitrogen-containing components derived from amino acid and protein, sugar, and a decomposition product thereof.

This refined raw material 1,4BG-containing solution can be converted by the refinement of the present invention to a high-quality biomass-derived 1,4BG capable of working out to a raw material of PBT with good color tone, but in order to obtain 1,4BG working out to a raw material of PBT with good color tone, it is preferable to reduce the carbonyl value of the refined raw material 1,4BG-containing solution.

The value of the carbonyl value of the refined raw material 1,4BG-containing solution is preferably 2.5 mgKOH/g or less, more preferably 2.0 mgKOH/g or less, still more preferably 1.5 mgKOH/g or less. As the value of carbonyl value is lower, the cost of refinement of the present invention can be reduced and this is economically preferred.

The refined raw material 1,4BG-containing solution here indicates the refined raw material 1,4BG immediately before passing through the steps (a) to (c) and in the case of passing through the later-described step (f), indicates the refined raw material 1,4BG immediately before passing through the step (f).

The method for reducing the carbonyl value in the refined raw material 1,4BG-containing solution is not particularly limited but includes, for example, a method where the carbonyl value is reduced in the process of biologically producing 1,4BG in the culture medium for organism fermentation, and a method where the carbonyl component is decreased together with water in the process of removing water contained in the 1,4BG-containing composition after separating and removing bacterial cells and salt contents from the fermentation culture medium. In the present invention, the carbonyl value in the refined raw material 1,4BG-containing solution is preferably reduced in at least one step of the later-described steps (b) to (d).

The method for measuring the carbonyl value is as described in Examples later.

The water concentration in the refined raw material 1,4BG-containing solution is not particularly limited, but usually, the upper limit is 20 mass % or less, preferably 18 mass % or less, more preferably 15 mass % or less. On the other hand, the lower limit is usually 0.01 mass % or more, preferably 0.02 mass % or more, more preferably 0.03 mass % or more. If the water concentration in the refined raw material 1,4BG-containing solution is too high, the temperature for steam recovery from the top region in a later step lowers and becomes improper. Also, if the water concentration in the refined raw material 1,4BG-containing solution is excessively reduced, the load of distillation for the removal of water is disadvantageously increased.

The refined raw material 1,4BG-containing solution here indicates the refined raw material 1,4BG immediately before passing through the steps (a) to (c) and in the case of passing through the later-described step (f), indicates the refined raw material 1,4BG immediately before passing through the step (f).

Incidentally, the water concentration in the refined raw material 1,4BG-containing solution introduced into the later-described step (a) is preferably 1.5 mass % or less, more preferably 1 mass % or less, still more preferably 0.5 mass % or less, yet still more preferably 0.2 mass % or less. Therefore, when the water concentration after removing water from the 1,4BG-containing composition is more than the upper limit above, it is preferable to reduce the water concentration by further repeating the same distillation as above.

The pH of the refined raw material 1,4BG-containing solution is preferably 5 or more, more preferably from 5.0 to 9.0, still more preferably from 5.2 to 8.0. A low pH of the refined raw material 1,4BG-containing solution means that the pH of the bottom liquid of the distillation column for the removal of water is low, and a problem of by-production of THF arises as described above. Also, if the pH of the refined raw material 1,4BG-containing solution is too high, that is, the pH of the bottom liquid of the distillation column for the removal of water is too high, a side reaction such as occurrence of high boiling is promoted as described above.

The 1,4BG concentration in the refined raw material 1,4BG-containing solution is not particularly limited, but usually, the lower limit is 80 mass % or more, preferably 82 mass % or more, more preferably 85 mass % or more. On the other hand, the upper limit is usually 99.5 mass % or less, preferably 99.0 mass % or less, more preferably 98.0 mass % or less. Although the concentration varies depending on the kind of the purity mixed and cannot be indiscriminately specified, with a concentration not more than the upper limit above, the load of the fermentation step is reduced, and 1,4BG having higher quality as a whole may be obtained.

In the present invention, a crude 1,4BG-containing solution is obtained from the refined raw material 1,4BG-containing solution by passing through at least one method out of a method where components higher in the boiling point than 1,4BG in the refined raw material 1,4BG-containing solution are removed through at least one or more steps of the following steps (a) to (c), a method where light-boiling-point components are removed, and a method where an unsaturated compound is converted to a hydride, and the crude 1,4BG-containing solution is refined through the following step (d), whereby high-purity refined 1,4BG is obtained.

Also, in the present invention, the following step (e) may be further performed, and the following step (f) may be performed in advance of the step (c).

Step (a):
A step of distilling the refined raw material 1,4BG-containing solution in a distillation column to remove components which are contained in the refined raw material 1,4BG-containing solution and higher in the boiling point than 1,4BG.

Step (b):
A step of distilling the refined raw material 1,4BG-containing solution in a distillation column to remove components which are contained in the refined raw material 1,4BG-containing solution and lighter in the boiling point than 1,4BG Step (c):
A hydrogenation step of at least partially converting unsaturated compounds contained in the refined raw material 1,4BG-containing solution into a hydride.

Step (d):
A step of distilling the crude 1,4BG-containing solution in a distillation column and withdrawing refined 1,4BG from a side stream.

Step (e):
A step of distilling components higher in the boiling point than 1,4BG, which are separated in the step (a), and thereby separating and recovering 1,4BG.

Step (f):
A step of brining the refined raw material 1,4BG-containing solution into contact with a base.

These steps (a) to (f) according to the present invention are described in detail below, but in the following description of each step, unless otherwise indicated, the distillation operation in a distillation column may be either a batch system or a continuous system, and in view of productivity, a distillation operation of a continuous system is preferred. Also, the distillation may be single stage distillation or multi-stage distillation but in view of separation performance, multi-stage distillation is preferred, and in the distillation column, either a plate or a regular and/or irregular packing material can be used.

The steps (a) to (c) are preceding steps before introducing the refined raw material 1,4BG-containing solution into the step (d), and the refined raw material 1,4BG is passed through any one step, two steps or all steps of the steps (a) to (c) and thereafter, introduced into the step (d). In the case of performing two or more steps out of the steps (a) to (c), the order of the steps is not particularly limited.

At the time of producing PBT by using, as a raw material, the refined 1,4BG obtained in the step (d), from the standpoint that coloring of the obtained PBT can be suppressed, the refined raw material 1,4BG-containing solution is preferably passed through all steps of the steps (a) to (c) and then introduced into the step (d). In this case, the order of respective steps may be shuffled, but the order is preferably step (a)→step (c)→step (b)→step (d).

FIG. 1 is a systematic diagram illustrating the order of steps when all of the steps (a) to (f) are employed, which is a preferred embodiment of the present invention.

The operation in each step is described below along with this systematic diagram, but the present invention is not limited to the embodiment shown in FIG. 1, and one or two steps out of the steps (a) to (c) or either one or more steps out of the steps (e) and (1) may be omitted, or other steps may be further added.

<Step (a): A Distillation Step for Removing the Components Higher in the Boiling Point than 1,4BG>

In the step (a), components (high-boiling component) higher in the boiling point than 1,4BG are removed from the refined raw material 1,4BG-containing solution in a distillation column (hereinafter, sometimes referred to as "distillation column (a)"), whereby a crude 1,4BG-containing solution free from high-boiling components is obtained as an overhead distillate of the distillation column (a).

As described above, the water concentration in the refined raw material 1,4BG-containing solution introduced into the distillation column (a) is preferably 1.5 mass % or less, more preferably 1 mass % or less, still more preferably 0.5 mass % or less, yet still more preferably 0.2 mass % or less. By setting the water concentration in the refined raw material 1,4BG-containing solution introduced into the distillation column (a) to be not more than the upper limit above, occurrence of a situation where steam cannot be recovered from a cooling condenser due to an excessive reduction in the top temperature of the distillation column can be advantageously prevented. Therefore, when the water concentration in the refined raw material 1,4BG-containing solution is more than the upper limit above, the refined raw material 1,4BG-containing solution is preferably introduced into the distillation column (a) after removing water by further repeating the distillation.

In the step (a), among others, nitrogen-containing components derived from amino acid and protein, and components higher in the boiling point than 1,4BG, which are peculiar to the fermentation process, such as sugar and a decomposition produce thereof, are removed.

The nitrogen-containing component such as amino acid is lightly boiled into amides, etc. by heating and, in particular, amides having a carbon number of 4, such as 2-pyrrolidone, are sometimes allowed to be contained. These amides also become causative of coloring at the time of PBT production and are preferably separated at the same time by this distillation operation.

Among others, in the case where 1,4BG as the PBT raw material contains 2-pyrrolidone, coloring at the time of PBT production becomes conspicuous. Therefore, the high-boiling-point components are removed until the 2-pyrrolidone concentration in the crude 1,4BG-containing solution that is the distillate of the distillation column (a) is reduced preferably to 100 ppm by mass or less, more preferably 20 ppm by mass or less, still more preferably 10 ppm by mass. On the other hand, the lower limit of the 2-pyrrolidone concentration in the distillate is preferably lower but is usually 0.01 ppm by mass or more, preferably 0.05 ppm by mass or more, more preferably 0.1 ppm by mass or more.

The concentration of the nitrogen atom-containing compound such as 2-pyrrolidone can be controlled by the nitrogen atom concentration, and although not particularly limited, the nitrogen atom concentration in the distillate is preferably 50 ppm by mass or less, more preferably 30 ppm by mass or less, still more preferably 20 ppm by mass or less.

The distillation column (a) used is preferably a distillation column having, as the theoretical plate, from 3 to 100 plates, more preferably from 5 to 50 plates.

The reflux ratio is arbitrary but is preferably from 0.01 to 100, more preferably from 0.1 to 50. Above all, a reflux ratio of 0.2 to 20 is preferred.

The reboiler as the heating region of the distillation column (a) is not particularly limited but is preferably a forced circulation reboiler or a falling film reboiler. In particular, the residence time in the contact region with a heating source in the bottom is preferably shorter so as to avoid fouling, and a structure where the heating source is not put into contact with a gas-phase part or a structure where the amount of contact is minimized, is preferred. It is also possible to recover steam from a cooling condenser in the top of the distillation column (a).

The top pressure of the distillation column (a) is, in terms of absolute pressure, preferably from 1 to 200 kPa, more preferably from 2 to 100 kPa, still more preferably from 5 to 50 kPa. As the top pressure is lower, the temperature in the column can be reduced, and production of new impurities from biomass-derived components such as amino acid and sugar can be thereby prevented. Also, as the top pressure is higher, steam recovery from the top region becomes more successful and furthermore, the volume of the column itself can be reduced.

The temperature in the distillation column (a) is determined by the composition and pressure, but the temperature in the bottom where the temperature becomes highest is preferably from 150 to 200° C., more preferably from 160 to 195° C., still more preferably from 165 to 190° C. By setting the bottom temperature of the distillation column (a) to be not less than the lower limit above, steam recovery from the top region can be prevented from failing due to too low temperature, and by setting the bottom temperature to be not more than the upper limit above, increase in the production volume of byproducts can be prevented.

The top temperature is preferably from 140 to 190° C., more preferably from 150 to 185° C., still more preferably from 155 to 180° C. By setting the top temperature to be not less than the lower limit above, steam recovery from the top region can be prevented from failing, and by setting the top temperature to be not more than the upper limit above, increase in the production volume of byproducts can be prevented.

The distillate obtained in the distillation column (a) of removing components higher in the boiling point than 1,4BG is carried over into the next step. The bottom product containing a large number of components higher in the boiling point than 1,4BG may be discarded as it is but is preferably fed to the distillation step (e) of recovering 1,4BG.

The fouling rate in the bottom of the distillation column (a) of removing components higher in the boiling point than 1,4BG can be greatly reduced by keeping the 1,4BG concentration in the bottom product of the distillation column (a) high, which contains a large number of components higher in the boiling point than 1,4BG. This is because excessive concentration of a high-boiling-point component promotes precipitation of amino acid, protein or a solid component such as sugar. Therefore, the bottom product withdrawn from the bottom of the distillation column (a) preferably contains 1,4BG to a certain extent, and the 1,4BG concentration in the bottom product is preferably from 40 to 99.2 mass %, more preferably from 50 to 99.0 mass %, still more preferably from 55 to 98.8 mass %.

Incidentally, the overhead distribution ratio (=(flow rate of overhead distillate/flow rate of feed)×100) in the distillation column (a) is preferably from 50 to 98%, more preferably from 60 to 95%, still more preferably from 70 to 90%.

Here, from the standpoint that 1,4BG contained in the components higher in the boiling point than 1,4BG, which are separated in the step (a), can be further recovered, the production method preferably further has the following step (e), in addition to the steps (a) to (d).

<Step (e): A Step of Separating and Recovering 1,4BG from the Components Higher in the Boiling Point than 1,4BG, which are Separated in the Step (a)>

In the step (e), the components higher in the boiling point than 1,4BG, which are separated in the step (a), that is, the distillate of the distillation column (a), are distilled in a distillation column (hereinafter, sometimes referred to as "distillation column (e)") to separate and recover 1,4BG.

The distillation column (e) used in the step (e) is preferably a distillation column having, as the theoretical plate, from 2 to 50 plates, more preferably from 5 to 30 plates.

The reflux ratio is arbitrary but is preferably from 0.01 to 100, more preferably from 0.1 to 50. Above all, a reflux ratio of 0.2 to 20 is preferred. It is also possible to recover steam from a cooling condenser in the top of the distillation column (e).

The reboiler as the heating region of the distillation column (e) is not particularly limited but is preferably a forced circulation reboiler or a falling film reboiler. In particular, the residence time in the contact region with a heating source in the bottom is preferably shorter so as to avoid fouling, and a structure where the heating source is not put into contact with a gas-phase part or a structure where the amount of contact is minimized, is preferred. Incidentally, unlike the distillation column (a) of the step (a), when the inside of the distillation column (e) of the step (e) is fouled, it is possible to once stop only the distillation column (e) and conduct a bypass operation all that time, even in the middle of continuous operation of the steps (a) to (d).

The top pressure of the distillation column (e) is, in terms of absolute pressure, preferably from 0.1 to 100 kPa, more preferably from 0.2 to 50 kPa, still more preferably from 1 to 20 kPa. As the top pressure is lower, the temperature in the column can be reduced, making it possible to prevent production of new impurities from biomass-derived components such as amino acid and sugar, and at the same time, obstruction due to progress of polymerization in the bottom can be avoided. Also, as the top pressure is higher, the volume of the column itself can be reduced.

The bottom temperature of the distillation column (e) is preferably from 150 to 200° C., more preferably from 160 to 195° C., still more preferably from 165 to 190° C. By setting the bottom temperature of the distillation column (e) to be not less than the lower limit above, steam recovery from the top region can be prevented from failing due to too low temperature, and by setting the bottom temperature to be not more than the upper limit above, the byproduct can be prevented from increasing in its production volume or becoming causative of fouling.

The top temperature is preferably from 140 to 190° C., more preferably from 150 to 185° C., still more preferably from 155 to 180° C. By setting the top temperature to be not less than the lower limit above, steam recovery from the top region can be prevented from failing due to too low temperature, and by setting the top temperature to be not more than the upper limit above, increase in the production volume of byproducts can be prevented.

The distillate containing 1,4BG separated in the distillation column (e) is preferably circulated to the distillation column (a) to recover 1,4BG. The bottom product containing a larger number of high-boiling point components concentrated in the distillation column (e) is discarded as it is but is preferably incinerated to recover heat.

Almost all high-boiling-point components can be discharged by this distillation operation, but a larger number of high-boiling-point components including 2-pyrrolidone can be further discarded when the distillation column (e) is set to have theoretical plates in the above-described range. In addition, a large amount of nitrogen contents or sulfur contents in the high-boiling-point components can be discharged.

<Step (c): A Step of Hydrogenating Unsaturated Compounds Contained in the Refined Raw Material 1,4BG-Containing Solution>

In the step (c), components causative of coloring of refined 1,4BG and/or components causative of coloring at the time of producing PBT by using the refined 1,4BG as a raw material are eliminated. Specifically, a carbonyl compound such as ketone, aldehyde and ester, an unsaturated compound having an olefin moiety, etc. are converted to hydrides by a hydrogenation reaction, resulting in disappearance of a carbonyl bond and an olefin moiety contained in the structures of compounds that are a causative component of coloring. The obtained hydrides can be removed as an alcohol, etc. by distillation.

Out of these causative components of coloring, a cyclic carbonyl compound having a carbon number of 5 or 6, such as ketone and/or aldehyde, exerts a significantly adverse effect on the color tone at the time of PBT production and therefore, in the step (c), the cyclic carbonyl compound having a carbon atom number of 5 or 6 is preferably converted to a hydride and reduced in its concentration, whereby a remarkable effect of improving the color tone at the time of PBT production is obtained. The "cyclic carbonyl compound having a carbon atom number of 5 or 6" as used herein indicates both a cyclic carbonyl compound having a carbon atom number of 5 and a cyclic carbonyl compound having a carbon atom number of 6.

Also, the total amount of these carbonyl compounds can be controlled as a carbonyl value, and the carbonyl value can be reduced in the step (c).

The cyclic carbonyl compound having a carbon atom number of 5 or 6 is preferably a compound having a 5-membered ring or 6-membered ring structure, more preferably having an oxygen atom-containing cyclic skeleton. Specifically, the compound includes one or more compounds selected from the group consisting of compounds having structures represented by the following formulae (I), (II) and (III):

[Chem. 1]

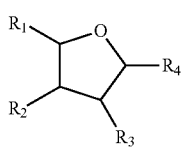

Formula (I)

(wherein in formula (I), each of $R_1$ to $R_4$ independently represents a hydrogen atom, a methyl group, a formyl group or an acetyl group, any one of $R_1$ to $R_4$ is a formyl group or an acetyl group, and the total number of carbon atoms contained in respective groups of $R_1$ to $R_4$ is 2 or less);

[Chem. 2]

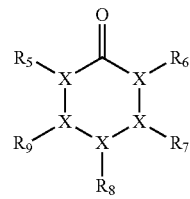

Formula (II)

(wherein in formula (II), each of a plurality of X independently represents a carbon atom or an oxygen atom, the total number of oxygen atoms contained in the plurality of X is 1, each of $R_5$ to $R_9$ independently represents a methyl group or a hydrogen atom, and the total number of carbon atoms contained in respective groups of $R_5$ to $R_9$ is 1 or less); and

[Chem. 3]

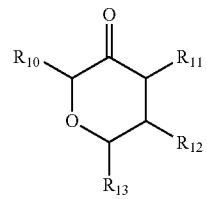

Formula (III)

(wherein in formula (III), each of $R_{10}$ to $R_{13}$ independently represents a methyl group or a hydrogen atom, and the total number of carbon atoms contained in respective groups of $R_{10}$ to $R_{13}$ is 1 or less).

More specifically, as examples of the compound having a structure represented by formula (I), the compound having a carbon atom number of 5 includes tetrahydro-2-furaldehyde, tetrahydro-3-furaldehyde and the like and the compound having a carbon atom number of 6 includes 2-acetyltetrahydrofuran[1-(tetrahydrofuran-2-yl)ethanone], 3-acetyltetrahydrofuran[1-(tetrahydrofuran-3-yl)ethanone], 5-methyltetrahydro-2-furaldehyde, 4-methyltetrahydro-2-furaldehyde, 3-methyltetrahydro-2-furaldehyde, 2-methyltetrahydro-3-furaldehyde, 4-methyltetrahydro-3-furaldehyde, 5-methyltetrahydro-3-furaldehyde, 2-(tetrahydrofuran-2-yl)acetaldehyde, 3-(tetrahydrofuran-2-yl)acetaldehyde, etc.

As examples of the compound having a structure represented by formula (II), the compound having a carbon atom number of 5 includes tetrahydro-4H-pyran-4-one and the like and the compound having a carbon atom number of 6 includes 3-methyltetrahydro-4H-pyran-4-one, 2-methyltetrahydro-4H-pyran-4-one, 2-formyl-tetrahydropyran, 3-formyl-tetrahydropyran, 4-formyl-tetrahydropyran, etc.

As examples of the compound having a structure represented by formula (III), the compound having a carbon atom number of 5 includes dihydro-2H-pyran-3(4H)-one and the like and the compound having a carbon atom number of 6 includes 2-methyldihydro-2H-pyran-3(4H)-one, 4-methyldihydro-2H-pyran-3(4H)-one, 5-methyldihydro-2H-pyran-3(4H)-one, 6-methyldihydro-2H-pyran-3(4H)-one, etc.

Preferably, as examples of the compound having a structure represented by formula (I), the compound having a carbon atom number of 5 is tetrahydro-2-furaldehyde, and the compound having a carbon atom number of 6 is 2-acetyltetrahydrofuran[1-(tetrahydrofuran-2-yl)ethanone], 3-acetyltetrahydrofuran[1-(tetrahydrofuran-3-yl)ethanone] or 5-methyltetrahydro-2-furaldehyde; as the compound having a structure represented by formula (II), the compound having a carbon atom number of 5 is tetrahydro-4H-pyran-4-one, and the compound having a carbon number of 6 is 2-methyltetrahydro-4H-pyran-4-one or 2-formyl-tetrahydropyran; and as the compound having a structure represented by formula (III), the compound having a carbon atom number of 5 is dihydro-2H-pyran-3(4H)-one, and the compound having a carbon atom number of 6 is 2-methyldihydro-2H-pyran-3(4H)-one, 4-methyldihydro-2H-pyran-3(4H)-one, 5-methyldihydro-2H-pyran-3(4H)-one or 6-methyldihydro-2H-pyran-3(4H)-one.

More preferably, as the compound having a structure represented by formula (I), the compound having a carbon atom number of 5 is tetrahydro-2-furaldehyde, and the compound having a carbon atom number of 6 is 2-acetyltetrahydrofuran[1-(tetrahydrofuran-2-yl)ethanone]; as the compound having a structure represented by formula (II), the compound having a carbon atom number of 5 is tetrahydro-4H-pyran-4-one, and the compound having a carbon number of 6 is 2-methyltetrahydro-4H-pyran-4-one; and as the compound having a structure represented by formula (III), the compound having a carbon atom number of 5 is dihydro-2H-pyran-3(4H)-one, and the compound having a carbon atom number of 6 is 2-methyldihydro-2H-pyran-3(4H)-one, 4-methyldihydro-2H-pyran-3(4H)-one or 5-methyldihydro-2H-pyran-3(4H)-one.

These cyclic carbonyl compounds having a carbon atom number of 5 or 6 are thought to be derived from sugar used as a raw material for the fermentation and is presumed to be produced in the fermentation step and/or refinement step by cyclization of polyhydric alcohols having a carbon atom number of 5 or 6 derived from pentose and/or hexose.

The concentration of the cyclic carbonyl compound having a carbon number of 5 or 6 is, in terms of the concentration in the solution introduced into the hydrogenation step (c), preferably from 0.001 to 2 mass %, more preferably from 0.01 to 1 mass %, still more preferably from 0.02 to 0.5 mass %. When the concentration of the cyclic carbonyl compound having a carbon number of 5 or 6 in the solution introduced into the hydrogenation step (c) is not more than the upper limit above, deterioration of the color tone at the time of PBT production is prevented. Also, in the case where the concentration is below the lower limit, although this is a preferred embodiment, the reaction conditions must be tightened and therefore, from the economical viewpoint, the concentration is preferably not less than the lower limit above.

The cyclic carbonyl compound having a carbon atom number of 5 or 6 is at least partially hydrogenated in the step (c), as a result, the UV absorption value is reduced and the carbonyl value is also reduced. Incidentally, in the step (c), at least 10% or more of the cyclic carbonyl compound having a carbon atom number of 5 or 6 is preferably hydrogenated, and this ratio is more preferably 20% or more, still more preferably 40% or more. Also, the concentration in the outlet solution of the hydrogenation step (c) is, as a total of cyclic carbonyl compounds having a carbon atom number of 5 or 6, preferably 0.1 mass % or less, more preferably 0.08 mass % or less.

The method for hydrogenation in the step (c) is not particularly limited, but the above-described causative component having a carbon atom number of 5 or 6, such as ketone, ester and aldehyde, can be hydrogenated in the presence of various hydrogenation catalysts. The hydrogenation catalyst is arbitrary as long as it is a catalyst capable of hydrogenating a cyclic carbonyl compound such as ketone and aldehyde, but it is preferable to use a solid catalyst containing at least one metal or two or more metals such as nickel (Ni), palladium (Pd), ruthenium (Ru), platinum (Pt) and copper (Cu), and a catalyst containing Ni is most preferred.

The amount of the metal such as Ni, Pd, Ru, Pt and Cu in the hydrogenation catalyst is preferably from 5 to 80 mass %, more preferably from 15 to 80 mass %, still more preferably from 50 to 80 mass %. Incidentally, the form of the metal contained in the hydrogenation catalyst may the metal itself or may be a metal oxide. In the case where the proportion of the metal oxide is high, a reductive activation treatment with a hydrogen gas may be previously performed before starting the reaction, but the reaction may be started without such a treatment.

The solid catalyst preferably contains a support, and the support includes silica, alumina, zirconia, kieselguhr and the like. Among others, the support preferably contains at least either kieselguhr or silica.

The content of the support in the catalyst is preferably from 5 to 95 mass %, more preferably from 7 to 80 mass %, still more preferably from 10 to 60 mass %.

As long as the solid catalyst for use in the present invention contains a metal such as Ni, Pd, Ru, Pt and Cu, the catalyst may contain other metals or metal oxides. For example, the catalyst may contain chromium, manganese, zinc, magnesium, sodium, rhenium and calcium, and in particular, a catalyst containing chromium and magnesium is preferred.

Such a metal may also be contained as the metal itself or in the state of various salts such as oxide and hydroxide. For example, the content of magnesium oxide in the catalyst is preferably from 0.1 to 20 mass %, more preferably from 0.5 to 15 mass %, still more preferably from 1 to 10 mass %. One of these catalysts may be used alone, or two or more thereof may be mixed and used.

The reaction temperature at the time of performing the hydrogenation of the step (c) is not particularly limited but is preferably from 0 to 200° C., more preferably from 30 to 150° C., still more preferably from 40 to 120° C. If this temperature is too high, catalyst deterioration is promoted, and furthermore, the amount of high-boiling byproducts is increased. If the reaction temperature is too low, the reaction scarcely proceeds.

The hydrogen pressure in the hydrogenation is not particularly limited but, in terms of gauge pressure, may be from 0.1 to 100 MPa and is preferably from 0.5 to 10 MPa, more preferably from 1 to 6 MPa. If this pressure is too low, the reaction rate is low and the productivity is reduced. If the pressure is too high, use of a reactor material in a large amount and increase in the load of compressor are involved, and the construction cost greatly rises.

The hydrogenation reaction is preferably performed by passing the refined raw material 1,4BG-containing solution (in FIG. 1, the solution obtained by further treating, in the step (f), the 1,4BG-containing distillate from the step (a)) to a reactor where a layer packed with the above-described solid catalyst is formed, and at this time, the reaction time is, in terms of residence time based on empty column, preferably 5 minutes or more, more preferably 10 minutes or more, still more preferably 30 minutes or more, and is preferably 100 hours or less, more preferably 50 hours or less, still more preferably 10 hours or less. If this residence time is too short, the reaction scarcely proceeds, and if the residence time is too long, the catalyst-packed layer becomes long and due to rise in the cost of installing the reactor and increase in the catalyst amount, the profitability significantly deteriorates.

As determined from the residence time based on empty column, the amount of the catalyst packed is, relative to the flow rate per minute of the solution introduced, preferably 0.05 volume times or more, more preferably 0.1 volume times or more, still more preferably 0.5 volume times or more, and is preferably 100 volume times or less, more preferably 50 volume times or less, still more preferably 10 volume times or less. If the amount of the catalyst packed is too small, the reaction scarcely proceeds, and if the amount of the catalyst packed is too large, the catalyst cost rises to significantly deteriorate the profitability.

As for the reaction mode, all of hydrogenation reactors of a general packed layer type using various solid catalysts, such as fixed bed, trickle bed, suspension bed (slurry) and multi-tubular system, may be used, but either a fixed bed reactor or a tickle bed reactor is preferred. As the reactor, one reactor may be used, or a plurality of reactors may be used. Also, a filter selected so as not to carry over the catalyst powder into later steps is preferably provided at the outlet of the hydrogenation reactor.

In the case where a large amount of a hydrogenation catalyst powder or a molten metal is carried over into later steps, a dehydrogenation reaction of 1,4BG may proceed in the heating region or the like to produce 2-hydroxytetrahydrofuran or 2-(4-hydroxybutyloxyl)tetrahydrofuran.

In the step (c), there is a fear of deterioration of the catalyst due to a long-term continuous operation. Among others, the impurities in the 1,4BG-containing composition produced by a fermentation process contain components including chlorine, sulfur and the like. In order to remove these chlorine and sulfur components, it is preferable to previously perform the following step (f) before the step (c).
<Step (f): A Step of Brining the Refined Raw Material 1,4BG-Containing Solution into Contact with a Base>

In the present invention, the above-described hydrogenation step (c) is preferably provided so as to remove cyclic carbonyl compounds having a carbon atom number of 5 or 6, which are a causative component of coloring, but as regards the hydrogenation catalyst, catalyst deterioration is accelerated by a strong acid such as hydrochloric acid and sulfuric acid. On the other hand, the crude 1,4BG-containing composition produced by a fermentation process sometimes contains chlorine contents such as hydrochloric acid, or sulfur contents such as sulfuric acid. Therefore, a step (f) of bringing a solid base or a soluble base such as amine into contact with the refined raw material 1,4BG-containing solution to remove those contents is preferably provided at a stage before passing through the step (c).

As the base usable in the step (f), a base that dissolves in the refined raw material 1,4BG-containing solution or crude 1,4BG-containing solution, such as various amines, may be used, and specifically, the base is preferably trimethylamine, triethylamine, tripropylamine, tributylamine, tripentylamine, trihexylamine, triheptylamine, trioctylamine, tridecanylamine, triphenylamine, diphenylmethylamine, diphenylethylamine, diphenylbutylamine, dimethylphenylamine, diethylphenylamine, dibutylphenylamine, tricyclopentylamine, tricyclohexylamine, tricycloheptylamine, pyridine, 1,4-diazabicyclo[2.2.2]octane, 1,8-diazabicyclo[5.4.0]-7-undecane, 1,5-diazabicyclo[4.3.0]-5-nonene, 2,5-diazabicyclo[2.2.1]heptane and the like, more preferably tributylamine, tripentylamine, trihexylamine, triheptylamine, trioctylamine, dimethylphenylamine, tricyclohexylamine, pyridine, 1,4-diazabicyclo[2.2.2]octane, 1,8-diazabicyclo[5.4.0]-7-undecane or 1,5-diazabicyclo[4.3.0]-5-nonene, still more preferably trioctylamine, pyridine, 1,8-diazabicyclo[5.4.0]-7-undecane or 1,4-diazabicyclo[2.2.2]octane.

However, in the step (f), a solid base capable of being easily separated after the contact with the refined raw material 1,4BG-containing solution or crude 1,4BG-containing solution is preferably used rather than a base that dissolves in the refined raw material 1,4BG-containing solution or crude 1,4BG-containing solution. The solid base can exert its effects and be used as long as it is a solid-form compound having basicity, but the base is preferably at least one member selected from an anionic exchange resin, a triazine ring-containing compound having an amino group or a substituted amino group, a polyamide, and an inorganic base.

The anionic exchange resin as the solid base is not particularly limited, and a commercially available product may be used. Also, the kind of the structure is not particularly limited, and all of a gel type, an MR (macroreticular) type, a porous type and a high porous type may be used, but among others, a styrene-based or acrylic resin having a quaternary ammonium salt as a functional group is preferred.

The triazine ring-containing compound having an amino group or a substituted amino group includes, preferably, a melamine resin, CTU guanamine (3,9-bis[2-(3,5-diamino-2,4-6-triazaphenyl)ethyl]-2,4,8,10-tetraoxaspiro[5,5]undecane), CMTU guanamine (3,9-bis[1-(3,5-diamino-2,4,6-triazaphenyl)methyl]-2,4,8,10-tetraoxaspiro[5,5]undecane) and the like. Two or more thereof may be used in combination.

The polyamide includes, for example, nylon 6, nylon 12, nylon 4/6, nylon 6/6, nylon 6/10, and nylon 6/12. Two or more thereof may be used in combination.

The inorganic base includes an alkali metal compound and an alkaline earth metal compound and specifically includes, for example, a metal oxide such as CaO and MgO, a metal hydroxide such as $Ca(OH)_2$ and $Mg(OH)_2$, a metal carbonate such as $Na_2CO_3$, $K_2CO_3$, $CaCO_3$ and $MgCO_3$, and a metal inorganic acid salt such as borate and phosphate of the compound above. Two or more thereof may be used in combination.

Among these solid bases, a triazine ring-containing compound having an amino group or a substituted amino group, and an anionic exchange resin are more preferred, and an anionic exchange resin is still more preferred.

In the step (f), the temperature at the time of contact of a base with the refined raw material 1,4BG-containing solution or crude 1,4BG-containing solution is preferably from −20 to 200° C., more preferably from 0 to 120° C., still more preferably from 30 to 100° C. If the temperature is too low, a special apparatus such as freezing device is necessary and the competitive power of the process is reduced, whereas if the temperature is too high, deterioration of the solid base proceeds.

The contact time is preferably from 1 minute to 100 hours, more preferably from 10 minutes to 20 hours, still more preferably from 20 minutes to 10 hours. If the contact time is too short, it is difficult to sufficiently remove the catalystdeteriorating component, whereas if the contact time is too long, the process becomes inefficient.

The solid base that is brought into contact with the refined raw material 1,4BG-containing solution or crude 1,4BG-containing solution may be used in a ratio of 0.01 to 100 in terms of the mass ratio to the refined raw material 1,4BG-containing solution or crude 1,4BG-containing solution, and the ratio is preferably from 0.1 to 20, more preferably from 0.2 to 10.

The contact method with the refined raw material 1,4BG-containing solution or crude 1,4BG-containing solution may be either in batch or continuous mode, but in view of ease of operation, a continuous flow system is particularly preferred.

<Step (b): A Distillation Step of Removing Components Lighter in the Boiling Point than 1,4BG>

In the step (b), the refined raw material 1,4BG-containing solution (in FIG. 1, the processing solution of the step (c)) is distilled in a distillation column (hereinafter, sometimes referred to as "distillation column (b)"), whereby components lighter in the boiling point than 1,4BG are removed. The components lighter in the boiling point than 1,4BG, which are removed in the distillation column (b), include causative components of coloring.

The purpose of this step (b) is both to sufficiently remove light-boiling-point components for obtaining high-purity 1,4BG and to remove a slight amount of causative components of coloring. By this operation, among others, a coloring-causative component itself, a hydrogenation form of the causative component of coloring, and furthermore, components lighter in the boiling point than 1,4BG, such as acetic acid, butyric acid, water, tetrahydrofuran, 2-hydroxytetrahydrofuran, gamma-butyrolactone, 1-acetoxy-4-hydroxybutane, 1,3-butanediol, 2,3-butanediol and 2-(4-hydroxybutyloxyl)tetrahydrofuran, are removed or quantitatively reduced.

In particular, as for the cyclic carbonyl compound having a carbon atom number of 5 or 6, which is a coloring-causative component described in the hydrogenation step of the step (c), in the case of performing the step (c) in advance of the step (b), most of the compound must be removed by the distillation of the step (b), and the concentration of the cyclic carbonyl compound having a carbon atom number of 5 or 6 in the bottom product of the distillation column (b) is preferably 100 ppm or less, more preferably 20 ppm or less, still more preferably 10 ppm or less, and it is particularly preferable to remove the compound to a concentration not more than the lower detection limit. The "not more than the lower detection limit" as used herein means a value detectable by a general gas chromatography. Specifically, the compound is preferably removed to a concentration of 2 ppm or less.

Also, the total amount of these carbonyl compounds can be controlled as a carbonyl value, and the carbonyl value can be reduced in the step (b).

In addition, the concentration of, among others, 1-acetoxy-4-hydroxybutane in the crude 1,4BG-containing solution after removing light-boiling components by the distillation column of the step (b), that is, in the bottom product of the distillation column (b), is preferably 50 ppm by mass or less, more preferably 30 ppm by mass or less, still more preferably 20 ppm by mass or less, and is preferably 0.1 ppm by mass or more, more preferably 0.2 ppm by mass or more, still more preferably 0.5 ppm by mass or more. By setting the 1-acetoxy-4-hydroxybutane concentration to be not more than the upper limit above, deterioration of the color tone at the time of PBT production can be prevented, and by setting the 1-acetoxy-4-hydroxybutane concentration to be not less than the lower limit above, high refinement such as increase of the reflux ratio is not required and this is economically advantageous.

The distillation column (b) used for removing the components lighter in the boiling point than 1,4BG is preferably a distillation column having, as the theoretical plate, from 5 to 100 plates, more preferably from 10 to 50 plates.

The reflux ratio is arbitrary but is preferably from 0.01 to 100, more preferably from 0.1 to 50. Above all, a reflux ratio of 0.2 to 20 is preferred.

The reboiler as the heating region of the distillation column (b) is not particularly limited but is preferably a forced circulation reboiler or a falling film reboiler. In particular, the residence time in the contact region with a heating source in the bottom is preferably shorter so as to avoid fouling, and a structure where the heating source is not put into contact with a gas-phase part or a structure where the amount of contact is minimized, is preferred. It is also possible to recover steam from a cooling condenser in the top of the distillation column (b).

The top pressure of the distillation column (b) is, in terms of absolute pressure, preferably from 1 to 200 kPa, more preferably from 2 to 100 kPa, still more preferably from 5 to 50 kPa. As the top pressure is lower, the temperature in the column can be reduced, and production of new impurities due to a reaction of impurities in the column can be thereby prevented. Also, as the top pressure is higher, steam recovery from the top region becomes more successful and furthermore, the volume of the column itself can be reduced.

The temperature in the distillation column (b) is determined by the composition and pressure, but the temperature in the bottom part where the temperature becomes highest is preferably 200° C. or less, more preferably 180° C. or less, still more preferably 170° C. or less, and is preferably 120° C. or more, more preferably 130° C. or more, still more preferably 140° C. or more. If the bottom temperature is too high, 1,4BG and a slight amount of impurities are reacted in the bottom to increase the fouling rate, and if the bottom temperature is too low, high vacuum is required, which is economically undesired.

The temperature in the top part where the temperature becomes lowest is 40° C. or more, more preferably 50° C. or more, still more preferably 60° C. or more. If the temperature of the top region is too low, the cooling cost becomes enormous. Furthermore, if the temperature is high both in the top part and in the upper part of the column, a cyclic carbonyl compound having a carbon atom number of 5 or 6, which is a causative component of coloring, is highly boiled with 1,4BG, and the highly boiled cyclic carbonyl compound having a carbon atom number of 5 or 6 is carried over in the high boiling form into the next step. In addition, if the temperature is high, the light-boiling-point component tends to be increased also in the bottom liquid. Therefore, the temperature in the top part is also preferably 160° C. or less, more preferably 140° C. or less, still more preferably 130° C. or less.

The bottom product obtained in the distillation column (b) of removing components lighter in the boiling point than 1,4BG is carried over into the next step. The distillate of the distillation column (b), containing a large number of components lighter in the boiling point than 1,4BG, may be discarded as it is, or light-boiling-point components may be further separated from the distillate and fed to a distillation step of recovering 1,4BG.

<Step (d): A Distillation Step of Obtaining Refined 1,4-Butanediol>

In the step (d), the crude 1,4BG-containing solution obtained through at least one step out of the steps (a) to (c) is distilled in a distillation column (hereinafter, sometimes referred to as "distillation column (d)"), and refined 1,4-butanediol is withdrawn as a product from a side stream. Depending on the case, the process sometimes passes through at least either one step of the steps (e) and (f), in addition to the steps (a) to (c).

In the step (d), the refined 1,4BG is obtained as a side stream of the distillation column (d), but 1,4BG containing a slight amount of light-boiling-point components such as acetic acid, butyric acid, water, tetrahydrofuran, 2-hydroxytetrahydrofuran, gamma-butyrolactone, 1-acetoxy-4-hydroxybutane, 1,3-butanediol, 2,3-butanediol and 2-(4-hydroxybutyloxyl)tetrahydrofuran is distilled out from the top of the distillation column (d), and 1,4BG containing a slight amount of high-boiling-point components is discharged from the bottom.

These overhead distillate and still bottom product of the distillation column (d) are preferably recovered to the preceding step individually or after being mixed. In particular, the coloring-causative component having a significant effect on the quality of the refined 1,4BG, such as cyclic carbonyl compound having a carbon atom number of 5 or 6, is a light-boiling-point component and therefore, is discharged in a higher concentration by the overhead distillate than by the side stream.

From the standpoint of decreasing the causative components of coloring, it is important that the gamma-butyrolactone concentration in the overhead distillate of the distillation column (d) is higher than the gamma-butyrolactone concentration in the refined 1,4BG withdrawn from a side stream. The gamma-butyrolactone concentration in the overhead distillate is preferably on the order of 1.1 to 500 times the gamma-butyrolactone concentration in the refined 1,4BG of the side stream. Also, the total amount of carbonyl compounds can be controlled as a carbonyl value, and the carbonyl value can be reduced in the step (d).

The concentration of the cyclic carbonyl compound having a carbon atom number of 5 or 6, in the refined 1,4BG withdrawn as a side stream, is preferably 20 ppm by mass or less, more preferably 12 ppm by mass or less, still more preferably 8 ppm by mass or less.

In addition, the water concentration and 1,4BG purity need to be controlled. Preferably, the water concentration in the side stream is 500 ppm by mass or less, and the 1,4BG purity is 99.5 mass % or more.

As long as the distillation column (d) is a distillation column capable of satisfying these quality items, refined 1,4BG can be obtained by performing distillation with arbitrary plates and conditions, but the distillation column (d) used to obtain refined 1,4BG is preferably a distillation column having, as the theoretical plate, from 5 to 100 plates, more preferably from 10 to 50 plates.

The side stream-withdrawing position when obtaining refined 1,4BG as a side stream is preferably located in the upper part relative to the raw material liquid feed plate and furthermore, in the height direction of the distillation column (b), the side stream is preferably withdrawn at a position superior to 50% of the height of the distillation column (b), for example, at a position of 50 to 90% of the theoretical plates from the bottom of the distillation column (b), based on the theoretical plates of the distillation column (b).

In particular, the distance between the raw material liquid feed plate and the side stream-withdrawing position is, in terms of the theoretical plate, 2 plates or more, preferably 3 plates or more, and, for example, is preferably from 3 to 20 plates. Incidentally, the number of theoretical plates from the top portion to the side stream-withdrawing position is preferably from 1 to 50, more preferably from 2 to 20, still more preferably from 3 to 10.

The reflux ratio of the distillation column (d) is arbitrary but is preferably from 0.01 to 100, more preferably from 0.1 to 50. Above all, a reflux ratio of 0.2 to 20 is preferred.

The reboiler as the heating region of the distillation column (d) is not particularly limited but is preferably a forced circulation reboiler or a falling film reboiler. In particular, the residence time in the contact region with a heating source in the bottom is preferably shorter so as to avoid fouling, and a structure where the heating source is not put into contact with a gas-phase part or a structure where the amount of contact is minimized, is preferred. It is also possible to recover steam from a cooling condenser in the top of the distillation column (d).

The top pressure of the distillation column (d) is, in terms of absolute pressure, preferably from 1 to 200 kPa, more preferably from 2 to 100 kPa, still more preferably from 2 to 50 kPa. As the top pressure is lower, the temperature in the column can be reduced, and production of new impurities due to a reaction of impurities in the column can be thereby prevented. On the other hand, as the top pressure is higher, steam recovery from the top region becomes more successful and furthermore, the volume of the column itself can be reduced.

The temperature in the distillation column (d) is determined by the composition and pressure, but the temperature in the bottom where the temperature becomes highest is preferably from 120 to 200° C., more preferably from 130 to 180° C., still more preferably from 140 to 170° C.

The temperature in the top part where the temperature becomes lowest is 40° C. or more, more preferably 50° C. or more, still more preferably 60° C. or more. If the bottom temperature is too high, 1,4BG and a slight amount of impurities may be reacted in the bottom to deteriorate the quality of the refined 1,4BG, and if the bottom temperature is too low, high vacuum is required, which is economically undesired.

Furthermore, if the temperature is high both in the top part and in the upper part of the column, a component such as acetal resulting from high boiling with 1,4BG of a cyclic carbonyl compound having a carbon atom number of 5 or 6, which is a causative component of coloring, may decompose to increase the concentration of the cyclic carbonyl compound having a carbon atom number of 5 or 6 in the refined 1,4BG. In addition, if the temperature is high, the light-boiling-point component tends to be increased also in the bottom liquid. Therefore, the temperature in the top part of the distillation column (d) is also preferably 160° C. or less, more preferably 150° C. or less, still more preferably 145° C. or less. If the temperature of the top region is too low, the cooling cost becomes enormous.

As described above, in the case of passing all of the steps (a) to (c), the order of the steps is not particularly limited, but from the standpoint that coloring can be suppressed at the time of producing PBT by using the refined 1,4BG as a raw material, the refined raw material 1,4BG-containing solution is preferably refined, as shown in FIG. 1, in order of the steps (a), (c) and (b) and then introduced into the step (d). The step (0 is not particularly limited as long as it is before the step (c), but the step is preferably immediately before the step (c).

The step (e) is preferably used together with the step (a). Incidentally, the loss of 1,4BG can be reduced by circulating the overhead distillate of the step (d) to the preceding stage of the step (0 and circulating the still bottom product to the step (e).

EXAMPLES

The present invention is described in greater detail below by referring to Examples, but the present invention is not limited to these Examples as long as the gist of the present invention is observed.

In the following, the analyses of 1,4-butanediol (1,4BG), tetrahydrofuran (THF), gamma-butyrolactone (hereinafter referred to as "GBL"), 1-acetoxy-4-hydroxybutane (hereinafter referred to as "14HAB"), 2-(4-hydroxybutyloxyl)tetrahydrofuran (hereinafter referred to as "BGTF"), 2-pyrrolidone (hereinafter referred to as "2P") and 2-hydroxytetrahydrofuran (hereinafter referred to as "OTF") were performed by gas chromatography in a gas chromatograph analyzer "Model Shimadzu GC-2014" manufactured by Shimadzu Corporation by using PEG-20M column (polar) manufactured by GL Science.

The concentrations of 1,4BG, THF, GBL, 14HAB, BGTF, 2P and OTF were calculated by the corrected area percentage method computed from the effective carbon coefficient by making a correction with the water amount according to the Karl Fisher's method (measured by "CA-03", manufactured by Mitsubishi Chemical Corporation).

Incidentally, the amount of the cyclic carbonyl compound having a carbon atom number of 5 or 6 is small and therefore, the sample was injected into the gas chromatograph analyzer without dilution by a solvent. Also, the amount of the cyclic carbonyl compound having a carbon atom number of 5 or 6 was calculated from the ratio between the area value of 1,4BG and the area value of the cyclic carbonyl compound without making a correction to the effective carbon coefficient.

The cyclic ketone and/or aldehyde each having a carbon atom number of 5 or 6 can be detected by GC-MS and/or GC-IR and can be discriminated from other components in the refined 1,4BG. These are presumed to be 2-acetyltetrahydrofuran and 2-methyldihydro-2H-pyran-3(4H)-one.

2-Acetyltetrahydrofuran (hereinafter, referred to as "ATF"):
  GC-MS (EI): 86, 71, 43, 29
  GC-IR: 2980, 2885, 1734, 1454, 1360, 1176, 1080, 925 cm$^{-1}$ 2-Methyldihydro-2H-pyran-3(4H)-one (hereinafter, referred to as "MHPO")
  GC-MS (EI): 114, 71, 42, 29
  GC-IR: 2956, 2851, 1742, 1240, 1115 cm$^{-1}$ In the following, the total of ATF and MHPO is defined as the total of cyclic carbonyl compounds having a carbon atom number of 5 or 6 and is referred to as "total $C_5,C_6$ cyclic carbonyl". Also, the component higher in the boiling point than 1,4BG is referred to as "high-boiling-point component", and the component lighter in the boiling point than 1,4BG is referred to as "light-boiling-point component".

The concentration in terms of nitrogen atom of a nitrogen-containing compound in the sample was determined by burning the sample in an argon/oxygen atmosphere and analyzing the combustion gas generated by means of a trace nitrogen analyzer (Model TN-10, manufactured by Mitsubishi Chemical Analytech Co., Ltd.) employing a combustion/reduced pressure chemiluminescence method.

As for the analysis of sulfur and chlorine concentrations in the sample, the sample was collected in a platinum-made boat and heated in a quartz-made tubular furnace ("Model AQF-100", manufactured by Mitsubishi Chemical Corporation) and after absorbing chlorine contents and sulfur contents in the combustion gas by an aqueous 0.03% hydrogen peroxide solution, the chloride ion and sulfate ion in the absorbing solution were measured by ion chromatograph ("Model ICS-1000", manufactured by Dionex) to determine the concentrations.

The absorbance of the sample at a measurement wavelength of 260 nm (hereinafter, simply referred to as "absorbance") was measured using "UV-2400" manufactured by Shimadzu Corporation (using a synthetic quartz-made closed cell having a light path length of 1 mm and a light path width of 10 mm) by a visible and ultraviolet spectroscopy. Here, pure water was used for blank measurement.

The carbonyl value of the sample was calculated according to the following formula by reacting a carbonyl compound with hydroxylamine hydrochloride (25° C., 1 hour) and quantitatively determining the produced hydrochloric acid by neutralization titration with N/10 methanolic KOH. For the titration, an automatic titrator (Automatic Titrator AUT-501, manufactured by DKK-Toa Corporation) was used.

$$\text{Carbonyl value (mgKOH/g)}=(A\times B)\times f\times 5.6/S$$

wherein A is the titer (mL) of 0.1 mol/L potassium hydroxide in this test, B is the titer (mL) of 0.1 mol/L potassium hydroxide in the blank test, f is the factor of 0.1 mol/L potassium hydroxide, and S is the sample amount (g).

Production of Refined Raw Material 1,4BG-Containing Solution

Production Example 1

A 1,4BG-containing composition was biologically produced in a culture medium for organism fermentation based on the description in JP-T-2010-521182. From this 1,4BG-containing composition, according to the method described in U.S. Patent Application Publication No. 2011/0003355, bacterial cells and salt contents were entirely or each at least partially removed by filtration, centrifugal separation and an ion exchange resin and then water was removed by distillation. The constituents of the 1,4BG-containing composition at this time are shown in Table-1. The pH of the 1,4BG-containing composition was 6.3.

In order to further separate water from the 1,4BG-containing composition, dehydration by distillation was performed using an Oldershaw distillation column having 30 theoretical plates. Here, while setting the top pressure of the distillation column to 10.8 kPa and the reflux ratio to 1.0 and controlling the top temperature and bottom temperature to become constant at 48° C. and 175° C., respectively, the 1,4BG-containing composition above was continuously introduced at the position of 20th plate counted from the bottom at a flow rate of 105 mL/hour, and water was distilled out from the top at a flow rate of 10 mL/hour. Simultaneously with distillation out of water, dehydrated crude 1,4BG-containing solution (refined raw material 1,4BG-containing solution) was continuously withdrawn as a bottom product from the bottom at 95 mL/hour. The water concentration in the refined raw material 1,4BG-containing solution was 0.025 mass % (250 ppm by mass). The constituents of the refined raw material 1,4BG-containing solution obtained are shown in Table-1. Incidentally, the pH of the refined raw material 1,4BG-containing solution was 5.5.

TABLE 1

| Component [unit] | 1,4BG-Containing Composition | Refined Raw Material 1,4BG-Containing Solution |
|---|---|---|
| Light-boiling-point component [ppm by mass] | 158 | 469 |
| ATF [ppm by mass] | 102 | 254 |
| MHPO [ppm by mass] | 118 | 477 |
| Water [mass %] | 9.3 | 0.025 |
| GBL [ppm by mass] | 103 | 137 |
| 14HAB [ppm by mass] | 184 | 191 |
| 1,4BG [mass %] | 90.3 | 99.4 |
| BGTF [ppm by mass] | 636 | 792 |
| High-boiling-point component [ppm by mass] | 2699 | 3430 |
| Nitrogen atom [ppm by mass] | 42 | 48 |
| Total $C_5$, $C_6$ cyclic carbonyl [ppm by mass] | 220 | 731 |

Refinement of Refined Raw Material 1,4BG-Containing Solution

Example 1

<Step (A): Distillation Separation of High-Boiling-Point Component>

With respect to the refined raw material 1,4BG-containing solution continuously obtained after the dehydration distillation in Production Example 1, components higher in the boiling point than 1,4BG, which are contained in the refined raw material 1,4BG-containing solution, were removed in a distillation column.

As the distillation column of the step (a), an Oldershaw distillation column having 30 theoretical plates was used. This Oldershaw distillation column is a distillation column where the heating source is put into contact substantially only with the bottom liquid and is not involved in contact with a gas-phase part, and the situation of being put into contact substantially only with the bottom liquid includes, for example, a state of allowing contact with a heating medium in a region below the gas-liquid interface in the bottom, and a state of eliminating a gas-phase part by spraying the bottom with a liquid, but the situation above is not limited to these embodiments.

While setting the top pressure to 15.7 kPa and the reflux ratio to 1.0 and controlling the top temperature and bottom temperature to become constant at 176° C. and 184° C., respectively, the refined raw material 1,4BG-containing composition was continuously introduced at the position of 10th plate counted from the bottom at a flow rate of 86 mL/hour. Continuous distillation out from the top part was performed at 74 mL/hour, and continuous withdrawal from the bottom was performed at 12 mL/hour. A continuous operation for 210 hours could be stably performed without production of a solid matter. A crude 1,4BG-containing solution after removing components higher in the boiling point than 1,4BG was obtained from the top (overhead distillate). The constituents of each of the still bottom product and the overhead distillate (crude 1,4BG-containing solution) of the distillation column (a) are shown in Table-2.

TABLE 2

| Component [unit] | Overhead Distillate | Still Bottom Product |
|---|---|---|
| Light-boiling-point component [ppm by mass] | 1255 | 191 |
| THF [ppm by mass] | 224 | 0 |
| Acetic acid [ppm by mass] | 10 | 0 |
| ATF [ppm by mass] | 291 | 24 |
| MHPO [ppm by mass] | 554 | 64 |
| OTF [ppm by mass] | 354 | 25 |
| Water [mass %] | 0.05 | 0.015 |
| GBL [ppm by mass] | 198 | 15 |
| 14HAB [ppm by mass] | 229 | 6 |
| 1,4BG [mass %] | 99.5 | 98.1 |
| BGTF [ppm by mass] | 1315 | 547 |
| 2P [ppm by mass] | 0 | 232 |
| High-boiling-point component [mass %] | 0.03 | 1.76 |
| Nitrogen atom [ppm by mass] | 9.3 | 250 |
| Total $C_5$, $C_6$ cyclic carbonyl [ppm by mass] | 845 | 88 |

Incidentally, in the step (a), distillation separation may be performed at a bottom temperature and a top temperature lower than respective temperatures above by reducing the top pressure of the distillation column (a), but by setting the bottom temperature and the top temperature high, heat recovery from the top part can be performed. In particular, the condensation heat of the distillate is preferably recovered as a pressurized steam. The recovered heat can be used for the heat source of other distillation columns and the like.

<Step (e): Recovery Distillation of 1,4BG from High-Boiling Point Components Separated in Step (a)>

Although an example by single stage distillation is described below, for more efficient 1,4BG recovery and separation of high-boiling-point components, continuous distillation is preferred, and more preferably, multi-stage distillation is performed. It is also preferable to appropriately conduct refluxing.

Into a 500 mL glass-made flask equipped with a glass-made condenser for distillation out, 252.4 g of the still bottom product (the constituents of the liquid are shown in the column of "Still Bottom Product" in Table-2) withdrawn from the bottom in the step (a) was charged, and single stage batch distillation was performed at a pressure of 4.9 kPa and an in-flask temperature of 153 to 169° C. As a result, a distillate containing 235.2 g of 1,4BG was separated and recovered. In the flask, 15.5 g of a concentrated liquid of high-boiling-point components was obtained as a distillation residue. The constituents of each of the separated and recovered distillate and the distillation residue are shown in Table-3.

TABLE 3

| Component [unit] | Distillate | Distillation Residue |
|---|---|---|
| Light-boiling-point component [ppm by mass] | 182 | 5111 |
| THF [ppm by mass] | 29 | 0 |
| Acetic acid [ppm by mass] | 208 | 2040 |
| ATF [ppm by mass] | 53 | 8 |
| MHPO [ppm by mass] | 135 | 33 |
| OTF [ppm by mass] | 15 | 5 |
| Water [mass %] | 0.015 | 0 |
| GBL [ppm by mass] | 70 | 0 |
| 14HAB [ppm by mass] | 6 | 0 |
| 1,4BG [mass %] | 99.8 | 30.5 |
| BGTF [ppm by mass] | 562 | 0 |
| 2P [ppm by mass] | 178 | 260 |
| High-boiling-point component [mass %] | 0.08 | 68.8 |
| Nitrogen atom [ppm by mass] | 59 | 4200 |
| Total $C_5$, $C_6$ cyclic carbonyl [ppm by mass] | 188 | 41 |

<Step (f): Contact Step of Crude 1,4BG-Containing Solution with Base>

A 100 mL-volume stainless steel-made reactor was filled with 85 mL of a weakly basic anion exchange resin (registered trademark: DIAION, Model WA20, a styrene-based resin having a quaternary ammonium salt as a functional group) (hereinafter, sometimes simply referred to as "WA20"), and the distillate (constituents of liquid: column of "Overhead Distillate" in Table-2) obtained in the step (a) above was continuously passed therethrough from the lower part of the reactor by an upward flow at 170 mL/hour, thereby performing a contact treatment. Incidentally, at the time of contact of the anion exchange resin with the distillate, the temperature was 40° C., and the pressure was ordinary pressure.

The chloride ion concentration (total chlorine concentration) and sulfide ion concentration (total sulfur concentration) in the distillate before contact with the anion exchange resin, and the chloride ion concentration (total chlorine concentration) and sulfide ion concentration (total sulfur concentration) in the distillate after contact with the anion exchange resin, which was obtained from the reactor outlet, were measured by an ion chromatograph, and the results thereof are shown in Table-4. In the Table, "WA20" indicates the above-described weakly basic anion exchange resin.

TABLE 4

| Component [unit] | Before Contact with WA20 | After Contact with WA20 |
| --- | --- | --- |
| Total sulfur concentration [ppm by mass] | 2 | 1.2 |
| Total chlorine concentration [ppm by mass] | 0.4 | 0.1 |

It is seen from Table-4 that the sulfur concentration and chlorine concentration in the crude 1,4BG-containing solution can be reduced by the step (f). The step (f) can reduce the catalyst deterioration rate of the catalyst used in the hydrogenation reaction of the next step (c) and can be expected to produce an effect of enhancing the catalyst life.

<Step (c): Hydrogenation Step of Crude 1,4BG-Containing Solution>

Step (c-1) Hydrogenation Reaction Catalyst: A Case of Kieselguhr-Supported Nickel-Chromium Catalyst (Continuous Flow Reactor)

A stainless steel-made flow reactor having a reaction volume of 120 mL was filled with 60 mL of a pellet-shaped kieselguhr-supported nickel-chromium catalyst (amount supported: 12 mass % of nickel, 1.5 mass % of chromium), and the crude 1,4BG-containing solution after contact with the anion exchange resin, which was obtained from the reactor outlet in the step (f), was passed therethrough at 30 mL/hour from the lower part of the reactor to perform a hydrogenation reaction of unsaturated compounds in the crude 1,4BG-containing solution.

Incidentally, the reactor was filled with the kieselguhr-supported nickel-chromium catalyst by providing, in order, a stainless steel-made filter, a glass bead layer, a catalyst layer, a glass bead layer and a stainless steel-made filter in the direction from the inlet to the outlet of the flow reactor. The reaction conditions of the hydrogenation reaction were set to a reaction temperature of 80° C. and a hydrogen pressure of 2.0 MPa (gauge pressure).

The crude 1,4BG-containing solution after the hydrogenation reaction was sampled with time from the reactor outlet and analyzed by gas chromatography and absorbance. The results are shown in Table-5.

TABLE 5

| Component [unit] | Before Hydrogenation Reaction | After Hydrogenation Reaction | Percentage Decrease |
| --- | --- | --- | --- |
| Light-boiling-point component [ppm by mass] | 169 | 981 | — |
| THF [ppm by mass] | 193 | 193 | — |
| Acetic acid [ppm by mass] | 4 | 4 | — |
| ATF [ppm by mass] | 477 | 281 | 41% |
| MHPO [ppm by mass] | 1044 | 574 | 45% |
| OTF [ppm by mass] | 490 | 753 | — |
| Water [mass %] | 0.053 | 0.134 | — |
| GBL [ppm by mass] | 263 | 248 | — |
| 14HAB [ppm by mass] | 261 | 266 | — |
| 1,4BG [mass %] | 99.3 | 99.3 | — |
| BGTF [ppm by mass] | 1455 | 1339 | — |
| 2P [ppm by mass] | 0 | 0 | — |
| High-boiling-point component [mass %] | 0.04 | 0.05 | — |
| Absorbance | 0.17 | 0.077 | 55% |
| Total $C_5$, $C_6$ cyclic carbonyl [ppm by mass] | 1521 | 855 | 44% |

It is seen from Table-5 that by passing the crude 1,4BG-containing solution through the step (c), a cyclic carbonyl compound having a carbon atom number of 5 or 6 is converted to a corresponding alcohol by hydrogenation. In addition, the absorbance was also reduced, and this reveals that the cyclic carbonyl compound having a carbon atom number of 5 or 6 is correlated with the coloring component for 1,4BG, particularly with the color tone b value at the time of PBT production, and the concentration of the coloring component can be reduced by the hydrogenation reaction.

Step (c-2) Hydrogenation Reaction Catalyst: A Case of Silica-Supported Nickel Catalyst (Batch Reactor)

A stainless steel-made autoclave having a reaction volume of 100 mL was filled with 2 g of a pellet-shaped silica-supported nickel catalyst (amount supported: a total of nickel and nickel oxide: 52 mass %), 40 g of the crude 1,4BG-containing solution resulting from contact with the anion exchange resin, which was obtained from the reactor outlet in the step (f), was placed therein, and the autoclave was then sealed at a hydrogen pressure of 0.99 MPa (gauge pressure) and shaken in an oil bath at 110° C. for 4 hours. Subsequent to the completion of reaction, the crude 1,4BG-containing solution after the hydrogenation reaction in the flask was sampled and analyzed by gas chromatography and absorbance. The results are shown in Table-6.

TABLE 6

| Component [unit] | Before Hydrogenation Reaction | After Hydrogenation Reaction | Percentage Decrease |
| --- | --- | --- | --- |
| Light-boiling-point component [ppm by mass] | 423 | 395 | — |
| THF [ppm by mass] | 0 | 0 | — |
| Acetic acid [ppm by mass] | 0 | 0 | — |
| ATF [ppm by mass] | 28 | 0 | 100% |
| MHPO [ppm by mass] | 76 | 21 | 72% |
| OTF [ppm by mass] | 77 | 56 | — |
| Water [mass %] | 0.061 | 0.098 | — |
| GBL [ppm by mass] | 34 | 44 | — |
| 14HAB [ppm by mass] | 29 | 66 | — |
| 1,4BG [mass %] | 99.8 | 99.8 | — |
| BGTF [ppm by mass] | 925 | 897 | — |
| 2P [ppm by mass] | 0 | 0 | — |
| High-boiling-point component [mass %] | 0.02 | 0.01 | — |
| Absorbance | 0.119 | 0.0494 | 59% |

TABLE 6-continued

| Component [unit] | Before Hydrogenation Reaction | After Hydrogenation Reaction | Percentage Decrease |
|---|---|---|---|
| Total $C_5$, $C_6$ cyclic carbonyl [ppm by mass] | 104 | 21 | 80% |

<Step (b): Distillation Separation of Light-Boiling-Point Component>

In separating light-boiling-point components from the crude 1,4BG-containing solution that was hydrogenated in the case of step (c-1), an Oldershaw distillation column having 30 theoretical steps was used. Distillation separation of light-boiling-point components was performed in the following three distillation condition cases.

Step (b-1): Standard Distillation Condition

While setting the top pressure to 4.0 kPa and the reflux ratio to 50.0 and controlling the top temperature and bottom temperature to constant temperatures of 139° C. and 163° C., respectively, the crude 1,4BG-containing solution (carbonyl value: 1.8 mgKOH/g) that was hydrogenated in the case of step (c-1) was continuously introduced at the position of 20th plate counted from the bottom at a flow rate of 110 mL/hour. Continuous distillation out from the top part was performed at 1.3 mL/hour, and continuous withdrawal from the bottom was performed at 108.7 mL/hour, thereby removing light-boiling-point components in the crude 1,4BG-containing solution. The constituents of each of the liquid distilled out from the top (overhead distillate) and the bottom product from the bottom part (still bottom product) are shown in Table-7.

Step (b-2): Enhanced Condition-1 for Removing Light-Boiling-Point Component

While setting the top pressure to 4.0 kPa and the reflux ratio to 50.0 and controlling the top temperature and bottom temperature to constant temperatures of 143° C. and 164° C., respectively, the crude 1,4BG-containing solution (carbonyl value: 1.8 mgKOH/g) that was hydrogenated in the case of step (c-1) was continuously introduced at the position of 20th plate counted from the bottom at a flow rate of 110 mL/hour. Continuous distillation out from the top part was performed at 5.4 mL/hour, and continuous withdrawal from the bottom was performed at 104.6 mL/hour, thereby removing light-boiling-point components in the crude 1,4BG-containing solution. The constituents of each of the liquid distilled out from the top (overhead distillate) and the bottom product from the bottom part (still bottom product) are shown in Table-7.

Step (b-3): Enhanced Condition-2 for Removing Light-Boiling-Point Component

While setting the top pressure to 4.0 kPa and the reflux ratio to 50.0 and controlling the top temperature and bottom temperature to constant temperatures of 145° C. and 165° C., respectively, the crude 1,4BG-containing solution (carbonyl value: 1.8 mgKOH/g) that was hydrogenated in the case of step (c-1) was continuously introduced at the position of 20th plate counted from the bottom at a flow rate of 110 mL/hour. Continuous distillation out from the top part was performed at 10.1 mL/hour, and continuous withdrawal from the bottom was performed at 100.2 mL/hour, thereby removing light-boiling-point components in the crude 1,4BG-containing solution. The constituents of each of the liquid distilled out from the top (overhead distillate) and the bottom product from the bottom part (still bottom product) are shown in Table-7.

Step (b-4): High-Temperature Condition

While setting the top pressure to 18.1 kPa and the reflux ratio to 50.0 and controlling the top temperature and bottom temperature to constant temperatures of 178° C. and 186° C., respectively, the crude 1,4BG-containing solution (carbonyl value: 1.8 mgKOH/g) that was hydrogenated in the case of step (c-1) was continuously introduced at the position of 20th plate counted from the bottom at a flow rate of 105 mL/hour. Continuous distillation out from the top part was performed at 10 mL/hour, and continuous withdrawal from the bottom was performed at 95 mL/hour, thereby removing light-boiling-point components in the crude 1,4BG-containing solution. The constituents of each of the liquid distilled out from the top (overhead distillate) and the bottom product from the bottom part (still bottom product) are shown in Table-7.

TABLE 7

| | Step (b-1) | | Step (b-2) | | Step (b-3) | | Step (b-4) | |
|---|---|---|---|---|---|---|---|---|
| Component [unit] | Overhead Distillate | Still Bottom Product | Overhead Distillate | Still Bottom Product | Overhead Distillate | Still Bottom Product | Overhead Distillate | Still Bottom Product |
| Light-boiling-point component [mass %] | 25.7 | 0.019 | 5.25 | 0.017 | 1.85 | 0 | 1.67 | 0.286 |
| THF [ppm by mass] | 808 | 5 | 291 | 4 | 1563 | 0 | 1330 | 4 |
| Acetic acid [ppm by mass] | 46 | 0 | 41 | 0 | 96 | 0 | 91 | 0 |
| ATF [ppm by mass] | 19161 | 0 | 4485 | 0 | 2056 | 0 | 1987 | 0 |
| MHPO [ppm by mass] | 143713 | 0 | 32946 | 0 | 3959 | 0 | 3845 | 0 |
| OTF [ppm by mass] | 5779 | 3 | 9212 | 0 | 2360 | 0 | 2189 | 0 |
| Water [mass %] | 8.672 | 0.004 | 2.359 | 0.004 | 0.495 | 0.003 | 0.468 | 0.004 |
| GBL [ppm by mass] | 35371 | 2 | 7089 | 3 | 3852 | 0 | 3970 | 19 |
| 14HAB [ppm by mass] | 25032 | 6 | 5196 | 2 | 2999 | 2 | 2877 | 7 |
| 1,4BG [mass %] | 22.9 | 99.8 | 77.8 | 99.8 | 95.5 | 99.9 | 96.2 | 99.5 |
| BGTF [ppm by mass] | 4912 | 1201 | 6069 | 1109 | 4622 | 1073 | 4622 | 1835 |
| 2P [ppm by mass] | 0 | 0 | 0 | 0 | 0 | 0 | 0 | 0 |
| High-boiling-point component [mass %] | 0.17 | 0.016 | 0.04 | 0.016 | 0.03 | 0.026 | 0.03 | 0.248 |
| Nitrogen atom [ppm by mass] | 680 | 5 | 140 | 4 | — | — | — | — |
| Total $C_5$, $C_6$ cyclic carbonyl [ppm by mass] | 162874 | 0 | 37431 | 0 | 6015 | 0 | 5832 | 0 |
| Carbonyl value (mgKOH/g) | 16.6 | 0.6 | — | — | — | 0.53 | — | — |
| Absorbance | 3.15 | 0.058 | 0.93 | 0.042 | — | 0.025 | — | — |

As apparent from Table-7, by performing distillation and separation of light-boiling-point components, a cyclic carbonyl compound having a carbon atom number of 5 or 6 can be removed from the crude 1,4BG-containing solution, and the absorbance and carbonyl value can be reduced.

In the step (d) described below, a cyclic carbonyl compound having a carbon atom number of 5 or 6 is regenerated from a part of light-boiling-point components and high-boiling-point components in the still bottom product in Table-7 and therefore, a cyclic carbonyl compound having a carbon atom number of 5 or 6, which is not present in the still bottom product, is mixed in the refined 1,4BG (Table-8 to Table-12).

Therefore, it is required not to carry over light-boiling-point components and high-boiling-point components into the step (d). It is seen from Table-7 that light-boiling-point components in the still bottom product can be sufficiently removed by increasing the amount of light-boiling-point components distilled out in the steps (b-2) and (b-3). In the case of high-temperature condition, a significant increase of high-boiling-point components is considered to occur in the upper part of the column as well as in the top part, and in the distillation under high-temperature condition of the step (b-4), a higher concentration of high-boiling-point components remain in the still bottom product. These high-boiling-point components are assumed to be acetals, ketals and hemiacetals of the cyclic carbonyl compound having a carbon atom number of 5 or 6. Therefore, distillation separation of light-boiling components at a lower temperature may be preferred.

<Step (d): Refinement Distillation of High-Purity 1,4-Butanediol>

In obtaining high-purity refined 1,4BG by distilling the crude 1,4BG-containing solution (the constituents of the liquid are shown in Still Bottom Product of Step (b-1) in Table-7) obtained in step (b-1) of the step (b) above, an Oldershaw distillation column having 25 theoretical plates was used. While setting the top pressure to 2.5 kPa and the reflux ratio to 10.0 and controlling the top temperature and bottom temperature to constant temperatures of 137° C. and 157° C., respectively, the crude 1,4BG-containing solution was continuously introduced at the position of 10th plate counted from the bottom at a flow rate of 76 mL/hour. At this time, a continuous operation for 55 hours was carried out by performing continuous distillation out from the top part at 1 mL/hour, continuous withdrawal of a side stream at 20th plate counted from the bottom at 73 mL/hour and continuous withdrawal from the bottom at 2 mL/hour. The constituents and absorbance of each of the overhead distillate, the side stream (refined 1,4BG) and the still bottom product are shown in Table-8.

Comparative Example 1

All were performed in the same manner except that in Example 1, refined 1,4BG was withdrawn from the top by not performing the withdrawal of a side stream in the step (d). The flow rate of the overhead distillate was 73 mL/hour. The results are shown in Table-8.

TABLE 8

| Component [unit] | Example 1 | | | Comparative Example 1 | |
| --- | --- | --- | --- | --- | --- |
| | Overhead Distillate | Side Stream (refined 1,4BG) | Still Bottom Product | Overhead Distillate | Still Bottom Product |
| Light-boiling-point component [ppm by mass] | 33 | 40 | 23 | 38 | 23 |
| THF [ppm by mass] | 17 | 3 | 15 | 10 | 15 |
| Acetic acid [ppm by mass] | 0 | 0 | 8 | 0 | 8 |
| ATF [ppm by mass] | 4 | 4 | 5 | 5 | 5 |
| MHPO [ppm by mass] | 12 | 6 | 3 | 7 | 3 |
| OTF [ppm by mass] | 92 | 72 | 7 | 78 | 7 |
| Water [ppm by mass] | 66 | 30 | 280 | 50 | 280 |
| GBL [ppm by mass] | 76 | 15 | 0 | 30 | 0 |
| 14HAB [ppm by mass] | 337 | 123 | 13 | 158 | 13 |
| 1,4BG [mass %] | 99.6 | 99.8 | 99.1 | 99.7 | 99.1 |
| BGTF [ppm by mass] | 2931 | 1222 | 255 | 1360 | 255 |
| 2P [ppm by mass] | 0 | 0 | 0 | 0 | 0 |
| High-boiling-point component [mass %] | 69 | 13 | 8800 | 15 | 8800 |
| Nitrogen atom [ppm by mass] | 17 | 3.2 | 46 | 3.4 | 46 |
| Total $C_5$, $C_6$ cyclic carbonyl [ppm by mass] | 16 | 10 | 8 | 12 | 8 |
| Absorbance | 0.058 | — | — | — | — |

Example 2

The operation was performed in the same manner as in Example 1 except that in the step (d), the top temperature and bottom temperature were controlled to constant temperatures of 137° C. and 158° C., respectively, the crude 1,4BG-containing solution was continuously introduced at the position of 10th plate counted from the bottom at a flow rate of 78 mL/hour, continuous distillation out from the top part was performed at 12 mL/hour, continuous withdrawal of a side stream at 20th plate counted from the bottom was performed at 64 mL/hour, and continuous withdrawal from the bottom was performed at 2 mL/hour. The constituents and absorbance of each of the overhead distillate, the side stream (refined 1,4BG) and the still bottom product are shown in Table-9.

TABLE 9

| | Example 2 | | |
|---|---|---|---|
| Component [unit] | Overhead Distillate | Side Strream (refined 1,4BG) | Still Bottom Product |
| Light-boiling-point component [ppm by mass] | 353 | 35 | 44 |
| THF [ppm by mass] | 16 | 8 | 11 |
| Acetic acid [ppm by mass] | 0 | 0 | 0 |
| ATF [ppm by mass] | 1 | 1 | 1 |
| MHPO [ppm by mass] | 3 | 3 | 8 |
| OTF [ppm by mass] | 29 | 11 | 0 |
| Water [ppm by mass] | 58 | 35 | 36 |
| GBL [ppm by mass] | 82 | 18 | 4 |
| 14HAB [ppm by mass] | 323 | 25 | 13 |
| 1,4BG [mass %] | 99.6 | 99.9 | 98.8 |
| BGTF [ppm by mass] | 2816 | 1123 | 248 |
| 2P [ppm by mass] | 0 | 0 | 0 |
| High-boiling-point component [ppm by mass] | 67 | 97 | 11711 |
| Nitrogen atom [ppm by mass] | — | 1.9 | — |
| Total $C_5$, $C_6$ cyclic carbonyl [ppm by mass] | 4 | 4 | 9 |
| Absorbance | — | 0.0076 | — |

Example 3

The operation was performed in the same manner as in Example 1 except that distillation was performed by using the still bottom product of step (b-2) of the step (b) (the constituents of the liquid are shown in Still Bottom Product of Step (b-2) in Table-7) as the raw material of the step (d) to obtain high-purity refined 1,4BG. The constituents and absorbance of each of the overhead distillate, the side stream (refined 1,4BG) and the still bottom product are shown in Table-10.

TABLE 10

| | Example 3 | | |
|---|---|---|---|
| Component [unit] | Overhead Distillate | Side Stream (refined 1,4BG) | Still Bottom Product |
| Light-boiling-point component [ppm by mass] | 318 | 82 | 44 |
| THF [ppm by mass] | 4 | 5 | 6 |
| Acetic acid [ppm by mass] | 0 | 0 | 0 |
| ATF [ppm by mass] | 3 | 4 | 3 |
| MHPO [ppm by mass] | 9 | 2 | 2 |
| OTF [ppm by mass] | 39 | 9 | 0 |
| Water [ppm by mass] | 218 | 65 | 216 |
| GBL [ppm by mass] | 48 | 16 | 2 |
| 14HAB [ppm by mass] | 312 | 22 | 13 |
| 1,4BG [mass %] | 99.7 | 99.8 | 98.6 |
| BGTF [ppm by mass] | 2619 | 1110 | 220 |
| 2P [ppm by mass] | 0 | 0 | 0 |
| High-boiling-point component [ppm by mass] | 90 | 24 | 14028 |
| Nitrogen atom [ppm by mass] | — | 1 | — |
| Total $C_5$, $C_6$ cyclic carbonyl [ppm by mass] | 12 | 6 | 5 |
| Absorbance | — | 0.0104 | — |

Example 4

The operation was performed in the same manner as in Example 1 except that distillation was performed by using the still bottom product of step (b-3) of the step (b) (the constituents of the liquid are shown in Still Bottom Product of Step (b-3) in Table-7) as the raw material of the step (d) to obtain high-purity refined 1,4BG The constituents of each of the overhead distillate, the side stream (refined 1,4BG) and the still bottom product are shown in Table-11.

TABLE 11

| | Example 4 | | |
|---|---|---|---|
| Component [unit] | Overhead Distillate | Side Stream (refined 1,4BG) | Still Bottom Product |
| Light-boiling-point component [ppm by mass] | 318 | 12 | 65 |
| THF [ppm by mass] | 13 | 3 | 2 |
| Acetic acid [ppm by mass] | 0 | 0 | 0 |
| ATF [ppm by mass] | 7 | 1 | 1 |
| MHPO [ppm by mass] | 2 | 1 | 2 |
| OTF [ppm by mass] | 114 | 6 | 0 |
| Water [ppm by mass] | 156 | 32 | 45 |
| GBL [ppm by mass] | 225 | 1 | 2 |
| 14HAB [ppm by mass] | 210 | 26 | 5 |
| 1,4BG [mass %] | 99.4 | 99.9 | 98.6 |
| BGTF [ppm by mass] | 2540 | 1100 | 223 |
| 2P [ppm by mass] | 0 | 0 | 0 |
| High-boiling-point component [ppm by mass] | 34 | 21 | 13552 |
| Nitrogen atom [ppm by mass] | — | 1 | — |
| Total $C_5$, $C_6$ cyclic carbonyl [ppm by mass] | 9 | 2 | 3 |
| Absorbance | 0.0227 | 0.0053 | — |

Reference Example 1

650 g of the still bottom product of step (b-3) of the step (b) (the constituents of the liquid are shown in Still Bottom Product of Step (b-3) in Table-7) was used as the raw material of the step (d), and the distillate was separated into a plurality of fractions by batch distillation under the condition of a top pressure of 0 to 0.9 kPa to obtain 3 lots of refined 1,4-butanediol. Of these lots, the constituents of the initially-obtained lot (Fr. 1, 147 g) are shown in Table-12.

TABLE 12

| Component [unit] | Reference Example 1 Fr. 1 Distillate |
|---|---|
| Light-boiling-point component [ppm by mass] | 191 |
| THF [ppm by mass] | 7 |
| Acetic acid [ppm by mass] | 0 |
| ATF [ppm by mass] | 6 |
| MHPO [ppm by mass] | 7 |
| OTF [ppm by mass] | 85 |
| Water [mass %] | 225 |
| GBL [ppm by mass] | 175 |
| 14HAB [ppm by mass] | 89 |
| 1,4BG [mass %] | 99.7 |
| BGTF [ppm by mass] | 2134 |
| 2P [ppm by mass] | 0 |
| High-boiling-point component [ppm by mass] | 32 |
| Nitrogen atom [ppm by mass] | 3.5 |
| Total $C_5$, $C_6$ cyclic carbonyl [ppm by mass] | 13 |

[Production of PBT]

In the production of PBT below, various analyses were performed by the following methods.

<Analysis of THF, Water>

A distillate in an esterification reaction was determined for water amount by the Karl Fisher's method (measured by "CA-03", manufactured by Mitsubishi Chemical Corporation), and the rest except for water was regarded as organic components. The THF amount in the organic components was determined by the above-described gas chromatography method and taken as the THF production volume. The THF production volume was expressed by mol % relative to terephthalic acid, and the obtained value was taken as the conversion ratio.

<Intrinsic Viscosity (IV) of PBT>

The intrinsic viscosity was determined using an Ubbelohde viscometer by the following procedure. That is, using a mixed solvent of phenol/tetrachloroethane (mass ratio: 1/1), the falling time in seconds was measured at 30° C. on a PBT solution having a concentration of 1.0 g/dL and on only the solvent, and the viscosity was determined according to the following formula:

$$IV=[(1+4K_H\eta_{sp})^{0.5}-1]/(2K_HC)$$

wherein $\eta_{sp}=(\eta/\eta_0)-1$, $\eta$ is the falling time in seconds of the PBT solution, $\eta_0$ is the falling time in seconds of the solvent, C represents the PBT concentration (g/dL) of the PBT solution, and $K_H$ is the Huggins' constant. A value of 0.33 was adopted for $K_H$.

<Terminal Carboxyl Group Concentration (Equivalent/Ton) of PBT>

0.5 g of PBT was dissolved in 25 mL of benzyl alcohol, the resulting solution was titrated using a 0.01 mol/L benzyl alcohol solution of sodium hydroxide, and the concentration was calculated according to the following formula:

Terminal carboxyl group concentration=$(A-B)\times 0.1\times f/W$ (equivalent/ton)

wherein A is the amount (μL) of the benzyl alcohol solution of 0.01 N sodium hydroxide required for titration, B is the amount (μL) of the benzyl alcohol solution of 0.01 mol/L sodium hydroxide required for titration of the blank, W is the amount (g) of the PBT sample, and f is the factor of the 0.01 mol/L sodium hydroxide <Color Tone b Value>

A columnar powder measurement cell having an inner diameter of 30 mm and a depth of 12 mm was filled with pellet-shaped PBT. Using a colorimeter, Color Meter ZE2000 (manufactured by Nippon Denshoku Industries Co., Ltd.), the color was measured in four places by the reflection method while rotating the measurement cell at every 90°, and the value was determined as a simple average value of the values obtained. The color tone was evaluated by the b value in the L, a, b color system. A lower value indicates that the color tone is better with less yellowing.

Production Example 2

PBT was produced by the following method using, as 1,4BG, the refined 1,4BG (the constituents of the liquid are shown in Side Stream of Example 1 in Table-8) obtained in Example 1.

A reaction vessel equipped with a stirring device, a nitrogen inlet, a heating device, a thermometer, a distillation tube and an exhaust port for evacuation was charged with 113 g of terephthalic acid, 183 g of 1,4BG and 0.7 g of a 1,4BG solution having previously dissolved therein 6 mass % of tetrabutyl titanate as a catalyst, and a nitrogen atmosphere was created inside the system by nitrogen-vacuum purging.

After warming the inside of the system to 150° C. with stirring, the temperature was raised to 220° C. over 1 hour under atmospheric pressure, and an esterification reaction was further performed for 2 hours while distilling out water produced.

Subsequently, 1.3 g of a 1,4BG solution of 1 mass % magnesium acetate tetrahydrate, obtained by dissolving magnesium acetate tetrahydrate in water and further dissolving the resulting solution in 1,4BG (mass ratio of magnesium acetate tetrahydrate, water and 1,4BG: 1:2:97), was added.

Thereafter, the temperature was held at 220° C. for 0.25 hours and then held until 245° C. over 0.75 hours. On the other hand, the pressure was reduced to 0.07 kPa over 1.5 hours from the initiation of polymerization, and a polycondensation reaction was performed for 0.8 hours under the same reduced pressure. The reaction system was returned to ordinary pressure to thereby complete the polycondensation. The obtained PBT was withdrawn as a strand from the bottom part of the reaction tank and passed under water at 10° C., and the strand was cult by a cutter to obtain pellet-shaped PBT.

The period from the initiation of pressure reduction after the addition of magnesium acetate to the completion of polycondensation was taken as the polycondensation time, and the intrinsic viscosity/polycondensation time was defined as the polycondensation rate. The polycondensation rate was 0.37 dL/g/hour. As for the THF conversion ratio, the THF amount was analyzed on a sample obtained by cooling and collecting a distillate during the esterification reaction by a dry ice trap, and the obtained value was expressed by mol % per terephthalic acid charged and found to be 57.0 mol %. The color tone b value of PBT was 2.7.

Production Example 3

PBT was produced by utterly the same method except that in Production Example 2, the refined 1,4BG obtained in Example 2 (the constituents are shown in Side Stream in Table-9) was used in place of the refined 1,4BG obtained in Example 1. The color tone b value of the obtained PBT was 2.2.

Production Example 4

PBT was produced by utterly the same method except that in Production Example 2, the refined 1,4BG obtained in Example 3 (the constituents are shown in Side Stream in Table-10) was used in place of the refined 1,4BG obtained in Example 1. The color tone b value of the obtained PBT was 1.7.

Production Example 5

PBT was produced by utterly the same method except that in Production Example 2, the refined 1,4BG obtained in Example 4 (the constituents are shown in Side Stream in Table-11) was used in place of the refined 1,4BG obtained in Example 1. The color tone b value of the obtained PBT was 1.6.

Production Example 6

PBT was produced by utterly the same method except that in Production Example 2, the refined 1,4BG obtained in Comparative Example 1 (the constituents are shown in Overhead Distillate of Comparative Example 1 in Table-8) was used in place of the refined 1,4BG obtained in Example 1. The color tone b value of the obtained PBT was 3.0.

Production Example 7

PBT was produced by utterly the same method except that in Production Example 2, the refined 1,4BG obtained in Reference Example 1 (the constituents are shown in Fr. 1 Distillate of Reference Example 1 in Table-12) was used in place of the refined 1,4BG obtained in Example 1. The color tone b value of the obtained PBT was 4.9.

The results of various analyses of Production Examples 2 to 7 are all shown in Table-13 together with the constituents of the refined 1,4BG used. Also, FIGS. 2 and 3 show, respectively, the relationship of the total $C_5,C_6$ cyclic carbonyl concentration in the raw material 1,4BG with the color tone b value at the time of production of PBT obtained and the relationship with the polycondensation rate.

Figure 2:
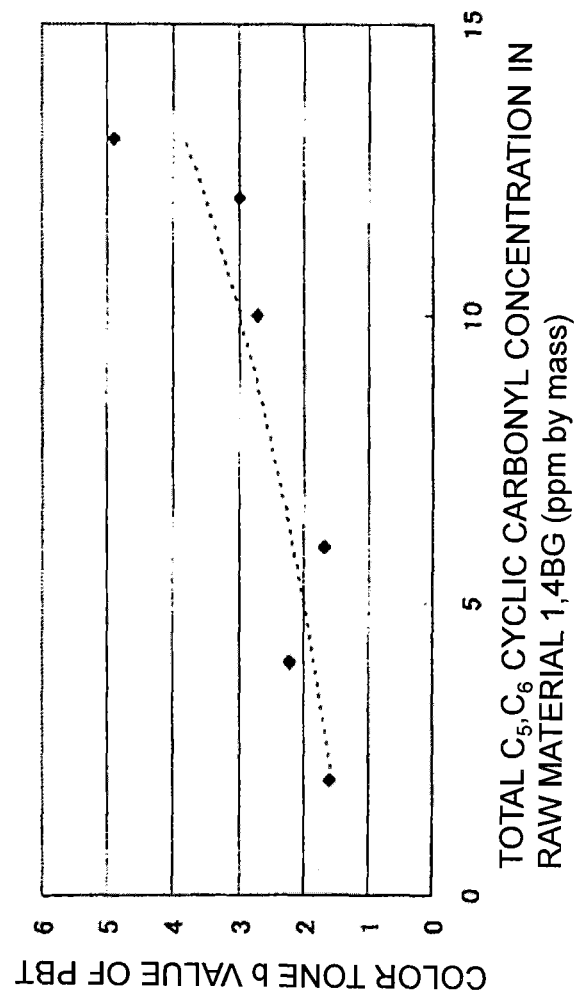
FIG. 2 is a graph showing the relationship between the total $C_5,C_6$ cyclic carbonyl concentration in 1,4BG and the color tone b value of PBT obtained using the 1,4BG.

It could be confirmed from Table-13 and FIG. 2 that when the total $C_5,C_6$ cyclic carbonyl concentration (total concentration of cyclic carbonyl compounds having a carbon atom number of 5 or 6) in the raw material 1,4-BG is 13 ppm, the color tone b value of PBT greatly increases. That is, removal of these cyclic carbonyl compounds having a carbon atom number of 5 or 6 is important for the production of PBT with good color tone.

Figure 3:
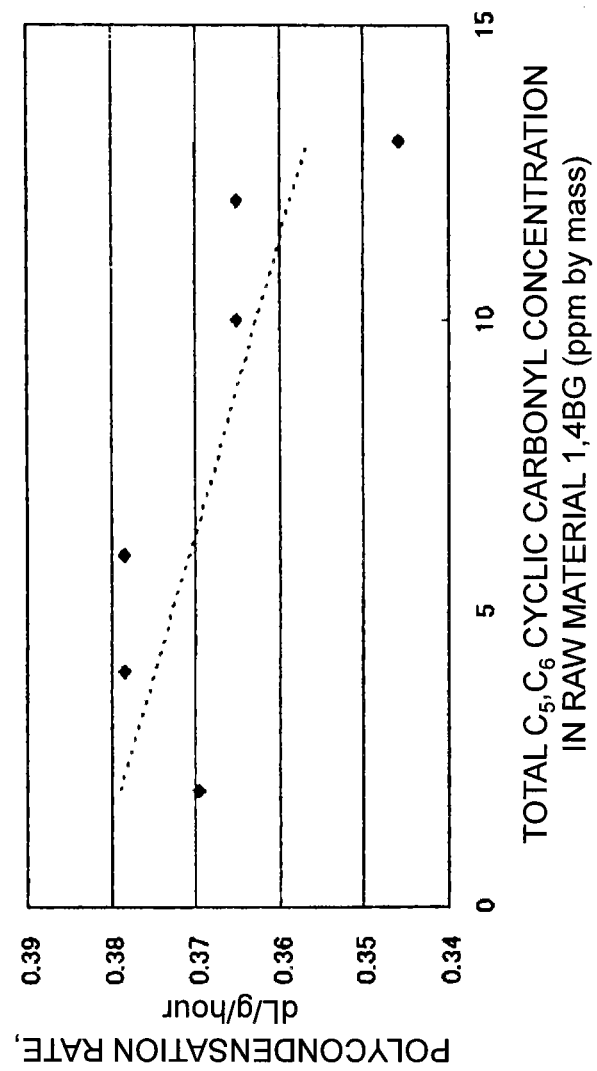
FIG. 3 is a graph showing the relationship between the total $C_5,C_6$ cyclic carbonyl concentration in 1,4BG and the polycondensation rate when producing PBT by using the 1,4BG.

It is seen from FIG. 3 that as the total $C_5,C_6$ cyclic carbonyl concentration (total concentration of cyclic carbonyl compounds having a carbon atom number of 5 or 6) in the raw material 1,4-BG is lower, the polycondensation rate (dL/g/hour) is more improved.

Examples 5 to 7

The same experiment as in Production Example 1 was performed three times, and dehydration distillation was conducted each time, whereby 3 lots of refined raw material 1,4BG-containing solution were produced (in Table-14, shown as "Crude 1,4BG). In each Example, refinement was performed in the same manner as in Example 1 except for using the 3 lots above as the raw material. The change in each of carbonyl value and absorbance among respective steps and the color tone of PBT produced in the same manner as in Production Example 2 by using the refined 1,4BG as the raw material are shown in Table-14.

TABLE 13

| | | Production Example 2 | Production Example 3 | Production Example 4 | Production Example 5 | Production Example 6 | Production Example 7 |
|---|---|---|---|---|---|---|---|
| Raw material 1,4BG | Kind | Example 1 | Example 2 | Example 3 | Example 4 | Comparative Example 1 | Reference Example 1 |
| | Nitrogen atom [ppm by mass] | 3.2 | 1.9 | 1 | 1 | 3.4 | 3.5 |
| | ATF [ppm by mass] | 4 | 1 | 4 | 1 | 5 | 6 |
| | MHPO [ppm by mass] | 6 | 3 | 2 | 1 | 7 | 7 |
| | Total $C_5, C_6$ cyclic carbonyl [ppm by mass] | 10 | 4 | 6 | 2 | 12 | 13 |
| | 1,4BG Purity [%] | 99.8 | 99.9 | 99.8 | 99.9 | 99.7 | 99.7 |
| | BGTF [ppm by mass] | 1222 | 1123 | 1110 | 1100 | 1360 | 2134 |
| | 14HAB [ppm by mass] | 123 | 25 | 22 | 26 | 158 | 89 |
| PBT Production conditions | Conversion ratio to THF [%] | 57.0 | 61.1 | 67.4 | 70.6 | 60.5 | 59.1 |
| | Polycondensation time [hr] | 2.3 | 2.3 | 2.3 | 2.3 | 2.3 | 2.4 |
| | Polycondensation rate [dL/g/hr] | 0.37 | 0.38 | 0.38 | 0.37 | 0.37 | 0.35 |
| | Intrinsic viscosity [dL/g] | 0.84 | 0.87 | 0.87 | 0.85 | 0.84 | 0.83 |
| Physical properties of PBT | Color tone b value | 2.7 | 2.2 | 1.7 | 1.6 | 3.0 | 4.9 |
| | Terminal carboxyl group concentration (equivalent/ton) | 5 | 7 | 8 | 7 | 5 | 4 |

TABLE 14

|  |  | Example 5 | Example 6 | Example 7 |
|---|---|---|---|---|
|  | Lot No. of rude 1,4BG | Lot 1 of Crude 1,4BG | Lot 2 of Crude 1,4BG | Lot 3 of Crude 1,4BG |
| Carbonyl value of 1,4BG (mg-KOH/g) | Crude 1,4BG (before dehydration) | 1.68 | 1.97 | 2.51 |
|  | Crude 1,4BG (after dehydration) | 1.47 | 1.53 | 2.12 |
|  | After separation of high-boiling component (step (a)) | 1.80 | 1.92 | 2.35 |
|  | After hydrogenation (step (c)) | 0.69 | 1.01 | 1.13 |
|  | After separation of light-boiling component (step (b)) | 0.05 | 0.13 | 0.14 |
|  | After final refinement distillation (step (d)) | 0.04 | 0.06 | 0.07 |
| Absorbance of 1,4BG | Crude 1,4BG (before dehydration) | 1.50 | 1.50 | 3.89 |
|  | Crude 1,4BG (after dehydration) | 2.71 | <5 | 3.64 |
|  | After separation of high-boiling component (step (a)) | 3.30 | 3.34 | 0.99 |
|  | After hydrogenation (step (c)) | 1.07 | 1.29 | 0.72 |
|  | After separation of light-boiling component (step (b)) | 0.55 | 0.64 | 0.56 |
|  | After final refinement distillation (step (d)) | 0.09 | 0.09 | 0.12 |
|  | Color tone b value of PBT | 1.9 | 2.1 | 2.6 |

It is seen from Table-14 that the carbonyl value of the refined 1,4BG can be reduced by reducing the carbonyl value of the crude 1,4BG and the color tone b value of the obtained PBT can be kept in a proper range by using a refined 1,4BG having a low carbonyl value. It is also seen that the carbonyl value of 1,4BG can be reduced by hydrogenation or distillation refinement. Furthermore, it is understood that when the carbonyl value of 1,4BG is reduced, the UV absorbance indicative of coloring of 1,4BG can also be reduced.

Distillation Experiment of Distillation Column of Step (a)

Reference Example 2

In the bottom region of the Oldershaw distillation column of the step (a) of Example 1, fouling sometimes proceeds due to precipitation of a solid matter. To avoid this problem, it is preferable to perform the distillation at a relatively low temperature of about 145° C. or not to heat the gas-phase part in the bottom that is a heating region. Specifically, the liquid level of the oil bath used as the heating source of the distillation column may be kept at a position lower than the liquid level of the bottom liquid pooling in the bottom part of the distillation column. On the other hand, as to heating of the gas-phase part, which promotes precipitation of a solid matter, for example, the liquid level of the oil bath may be kept higher than the bottom liquid pooling in the bottom part of the distillation column so as to keep, in addition to the bottom liquid, the wall temperature of the gas-phase part in the bottom part at a temperature close to that of the heating source.

In the following, a distillation experiment was performed in three cases, a case where the gas-phase part is heated at a high temperature (245° C.) by changing the position of the liquid level of an oil bath as a heating source in the bottom part of the distillation column of the step (a) of Example 1, a case where the gas-phase part is heated under the low temperature condition of 145° C., and a case where heating is performed at a high temperature (245° C.) but the gas-phase part is not heated. The results are shown in Table-15. Incidentally, the liquid introduced is the refined raw material 1,4BG-containing solution having the constituents shown in Table-1.

TABLE 15

|  | Unit | High-Temperature Distillation, gas-phase part was not heated | High-Temperature Distillation, gas-phase part was heated | Low-Temperature Distillation |
|---|---|---|---|---|
| Heating source temperature of distillation column | ° C. | 245 | 245 | 190 |
| Bottom temperature of distillation column | ° C. | 184 | 184 | 145 |
| Operation time | hr | 210 | 55 | 55 |
| Amount of solid matter precipitated | mg | 0.2 | 17 | 0.1 |
| Cumulative amount of 1,4BG processed | g | 17,534 | 4,592 | 4,592 |
| Amount of solid matter precipitated/amount of 1,4BG processed | ppm by mass | 0.01 | 4 | 0.02 |

As apparent from Table-15, compared with a case where the gas-phase part is heated at a high temperature, the amount of a solid matter precipitated can be greatly reduced by creating a low-temperature condition of 145° C. or the like or a condition where the gas-phase part is not heated despite high temperature.

Incidentally, as for the distillation column of the step (a) in the process on an industrial scale, in order not to heat the gas-phase part, it is preferable to use, as the heating source, a forced circulation reboiler or a falling film reboiler. Above all, a force circulation reboiler is more preferred, because the liquid phase can be more completely held by using a back pressure valve at the outlet of the heat exchanger and thereby increasing the pressure inside of the heat exchanger.

Hydrogenation Reaction of Chlorine-Containing Solution

Reference Example 3

In 1,4BG produced by Mitsubishi Chemical Corporation, 10 mass % of 1,4-dihydroxy-2-butene that is a reagent produced by TCI, was dissolved. In the resulting solution, the total chlorine concentration was 79 ppm by mass, and the total sulfur concentration was 0.1 ppm by mass. A hydrogenation experiment was performed using this solution under the same reaction conditions as in step (c-1) of Example 1 except that the reaction temperature was set to 100° C. and the hydrogen pressure was set to 3.5 MPa (gauge pressure), as a result, very rapid progress of catalyst deterioration was confirmed as shown in Table-16 (no WA20 treatment).

On the other hand, a solution obtained by subjecting the solution having a total chlorine concentration of 79 ppm by mass and a total sulfur concentration of 0.1 ppm by mass to a treatment with an anion exchange resin (WA20) corresponding to the step (f) under the conditions that the amount of ion exchange resin used was 300 mL, the treatment flow rate was 215 g/hour and the contact temperature was 55° C., came to have a total chlorine concentration of 0.1 ppm by mass and a total sulfur concentration <0.1 ppm by mass (below the detection limit), and a hydrogenation experiment was performed on this treated solution under the same hydrogenation conditions as above. Then, catalyst deterioration was not confirmed as shown in Table-16 (treated with WA20).

The Ni concentration in liquid in the course of flow evaluation was analyzed and compared by ICP-OES, as a result, in the solution treated with WA20, the Ni concentration in liquid was below the detection limit even after the reaction, but in the solution not treated with WA20, an Ni concentration of 5 ppm by mass was detected.

In Solution Before Hydrogenation Reaction of Table-5, the chlorine concentration is about 0.4 ppm by masse, but considering a long-term operation, it is understood that in addition to an anion exchange resin such as WA20, a solid base or soluble bases such as various amines, elution of a catalyst component by an acid is preferably avoided.

TABLE 16

| Conditions | Cumulative Reaction Time (hr) | Conversion Ratio of 1,4-Dihydroxy-2-Butene (%) | Selectivity Ratio of 1,4-Butanediol (%) | Ni Elution Concentration (ppm) |
|---|---|---|---|---|
| Treated with WA20 | 22 | 98.7 | 99.5 | — |
|  | 94 | 98.8 | 99.6 | <0.5 |
|  | 118 | 98.9 | 99.6 | — |
|  | 143 | 98.7 | 99.6 | — |
|  | 166 | 98.8 | 99.6 | — |
|  | 190 | 98.8 | 99.5 | <0.5 |

TABLE 16-continued

| Conditions | Cumulative Reaction Time (hr) | Conversion Ratio of 1,4-Dihydroxy-2-Butene (%) | Selectivity Ratio of 1,4-Butanediol (%) | Ni Elution Concentration (ppm) |
|---|---|---|---|---|
| No WA20 treatment | 18 | 99.7 | 83.7 | — |
|  | 42 | 99.4 | 78.2 | — |
|  | 66 | 99.0 | 79.3 | — |
|  | 90 | 97.9 | 77.4 | — |
|  | 162 | 96.9 | 79.3 | 5 |
|  | 186 | 96.3 | 79.2 | — |
|  | 210 | 95.4 | 81.4 | — |
|  | 258 | 93.9 | 83.5 | — |
|  | 329 | 92.0 | 74.6 | — |

Side Stream Effect of Fossilization Process

Reference Example 4

Butadiene, acetic acid and oxygen were continuously reacted at a pressure of 6 MPa and a temperature of 60 to 99° C. in the presence of a catalyst containing palladium and tellurium supported on silica. As the oxygen, air diluted with nitrogen (oxygen concentration: 21 vol %) was used. Acetic acid and high-boiling matters were removed by distilling the reaction solution to obtain a reaction product mainly composed of diacetoxybutene.

This reaction product was continuously fed together with hydrogen to a front-stage hydrogenation reactor filled with a catalyst containing palladium supported on activated carbon and a rear-stage reactor filled with a catalyst containing ruthenium supported on silica, thereby effecting hydrogenation. The front-stage hydrogenation reaction of saturating a carbon-carbon double bond was performed at a pressure of 2 MPa and a temperature of 40 to 70° C., and the rear-stage hydrogenation reaction of causing hydrogenation of an aldehyde group or hydrogenolysis of an acetal compound was performed at a pressure of 2 MPa and a temperature of 90 to 110° C.

The hydrogenated reaction product obtained above was passed as a mixed solution with water at 40 to 60° C. through a hydrolysis reactor filled with DIAION SK1B (a product of Mitsubishi Chemical Corporation, sulfonic acid-type cation exchange resin, DIAION is a registered trademark of the same company) to undergo a hydrolysis reaction. The obtained hydrolysis reaction solution was continuously distilled at a bottom temperature of 158° C. and a top pressure of 15 kPa to distill out water and acetic acid from the top and obtain a bottom liquid from the bottom. The bottom liquid was continuously distilled at a bottom temperature of 191° C., a top pressure of 21 kPa and a reflux ratio of 30 by using a distillation column having a number of theoretical plates of 100 and thereby divided into three streams of overhead liquid, side stream, and bottom liquid.

The bottom stream obtained above was continuously fed together with hydrogen at a pressure of 0.9 MPa and a temperature of 100° C. to a reactor filled with a catalyst containing palladium supported on activated carbon to perform hydrogenolysis of an acetal compound and the like. The resulting reaction solution was continuously distilled at a bottom temperature of 181° C., a top pressure of 20 kPa and a reflux ratio of 0.62 by using a distillation column having a number of theoretical plates of 10 (=second distillation).

The reaction product was fed to 3rd plate counted from the top, water and tetrahydrofuran were distilled out from the top, and a bottom liquid containing 1,4-butanediol and high-boiling-point matters was obtained from the bottom. This bottom liquid was then continuously distilled at a bottom temperature of 160° C., a top pressure of 5.7 kPa and a reflux ratio of 0.65 by using a packed column having a number of theoretical plates of 20 (=third distillation).

The bottom liquid was fed to 12th plate counted from the top, 1,4-butanediol was distilled out from the top, and high-boiling-point maters were flowed out as a mixture with 1,4-butanediol from the bottom. The weight ratio of the overhead distillate and the bottom distillate was 98:2. The 1,4-butanediol obtained above was continuously fed to 9th plate counted from the top of a packed column having a number of theoretical plates of 20 and distilled at a bottom temperature of 160° C., a top pressure of 5.7 kPa and a reflux ratio of 63, 1,4-butanediol containing 1,4-butanediol monoacetate was distilled out from the top, high-purity refined 1,4-butanediol was obtained as the product from the side stream, and 1,4-butanediol containing high-boiling-point components was withdrawn from the bottom (=fourth distillation). The weight ratio of the overhead distillate and the side stream was 1:99.

Reference Example 5

PBT was produced by utterly the same method except that in Production Example 2, the refined 1,4BG (side stream) obtained in Reference Example 4 was used in place of the refined 1,4BG obtained in Example 1. The color tone b value of the obtained PBT was 1.4.

Reference Example 6

PBT was produced by utterly the same method except that in Production Example 2, 1,4BG obtained by adding 1% of the top liquid in the fourth distillation to the refined 1,4BG (side stream) obtained in Reference Example 4 was used in place of the refined 1,4BG obtained in Example 1. The color tone b value of the obtained PBT was 2.0.

It is seen from Reference Examples 5 and 6 and Examples above that even in the production of 1,4BG by a bio-process, a PBT color tone at a level equivalent to that in the fossilization process can be achieved by withdrawing a side stream.

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2012-128065) filed on Jun. 5, 2012 and Japanese Patent Application (Patent Application No. 2013-037301) filed on Feb. 27, 2013, the contents of which are incorporated herein by way of reference.

The invention claimed is:

1. A method for producing refined 1,4-butanediol having a concentration of a cyclic carbonyl compound having a carbon atom number of 5 or 6 of 12 ppm by mass or less, comprising biologically producing 1,4-butanediol in a culture medium for fermentation of an organism capable of producing 1,4-butanediol, at least partially removing each of a bacterial cell, a salt content and water from said fermentation culture medium to obtain a refined raw material 1,4-butanediol-containing solution, obtaining therefrom a crude 1,4-butanediol-containing solution through the following steps (b') and (c) and optionally the following steps (a) and (b), refining said crude 1,4-butanediol-containing solution through the following step (d) and obtaining said refined 1,4-butanediol having a concentration of a cyclic carbonyl compound having a carbon atom number of 5 or 6 of 12 ppm by mass or less:

Step (a):
    a step of distilling said refined raw material 1,4-butanediol-containing solution in a distillation column to remove components which are contained in said refined raw material 1,4-butanediol-containing solution and higher in the boiling point than 1,4-butanediol;

Step (b):
    a step of distilling said refined raw material 1,4-butanediol-containing solution in a distillation column to remove components which are contained in said refined raw material 1,4-butanediol-containing solution and lower in the boiling point than 1,4-butanediol;

Step (b'):
    a step of bringing said refined raw material 1,4-butanediol-containing solution, optionally after treatment in one or both of steps (a) and (b), into contact with a base;

Step (c):
    a hydrogenating step of at least partially converting unsaturated compounds contained in said refined raw material 1,4-butanediol-containing solution obtained from step (b') into a hydride via hydrogenation; and Step (d):
    a step of distilling said crude 1,4-butanediol-containing solution in a distillation column, withdrawing the refined 1,4-butanediol from a side stream and obtaining said refined 1,4-butanediol having a concentration of a cyclic carbonyl compound having a carbon atom number of 5 or 6 of 12 ppm by mass or less.

2. The method as claimed in claim 1, wherein the concentration of a cyclic carbonyl compound having a carbon atom number of 5 or 6 in the refined 1,4-butanediol obtained in said step (d) is 2-10 ppm by mass.

3. The method as claimed in claim 1, comprising step (a) and further comprising the following step (e):

Step (e):
    a step of distilling components higher in the boiling point than 1,4-butanediol, which are separated in said step (a), in a distillation column and thereby separating and recovering 1,4-butanediol.

4. The method as claimed in claim 1, wherein the water concentration in the refined raw material 1,4-butanediol-containing solution immediately before passing through any one step of said steps (a) to (c) or through the step (b') is from 0.01 to 20 mass % and the pH thereof is 5 or more.

5. The method as claimed in claim 1, wherein in the hydrogenation step of said step (c), hydrogenation is performed using a solid catalyst having a nickel-containing metal supported on at least either kieselguhr or silica.

6. The method as claimed in claim 1, wherein the base in said step (b') is a solid base.

7. The method as claimed in claim 1, comprising said step (b), wherein the components lower in the boiling point than 1,4-butanediol in said step (b) contain 1-acetoxy-4-hydroxybutane and the 1-acetoxy-4-hydroxybutane concentration in the crude 1,4-butanediol-containing solution after the removal of said components lower in the boiling point than 1,4-butanediol is from 0.1 to 50 ppm by mass.

8. The method as claimed in claim 1, comprising said step (b), wherein a bottom temperature of the distillation column in said step (b) is from 120 to 200° C.

9. The method as claimed in claim 1, comprising said step (a), wherein a bottom temperature of the distillation column in said step (a) is from 150 to 200° C.

10. The method as claimed in claim 1, comprising said step (a), wherein the components higher in the boiling point than 1,4-butanediol in said step (a) contain 2-pyrrolidone and the 2-pyrrolidone concentration in the crude 1,4-butanediol-containing solution after the removal of said components higher in the boiling point than 1,4-butanediol is 20 ppm by mass or less.

11. The method as claimed in claim 1, comprising said step (a), wherein a heating source of the distillation column in said step (a) contacts substantially only with a bottom liquid but involves no contact with a gas-phase part.

12. The method as claimed in claim 1, wherein a gamma-butyrolactone concentration in the overhead distillate of the distillation column in said step (d) is higher than the gamma-butyrolactone concentration in the refined 1,4-butanediol withdrawn from a side stream.

13. The method as claimed in claim 1, comprising a step of controlling the carbonyl value in the refined raw material 1,4-butanediol-containing solution immediately before passing through any one step of said steps (a) to (c) or through the step (b'), to be 2.5 mgKOH/g or less.

14. The method as claimed in claim 1, wherein in at least one step of said steps (b) to (d), the carbonyl value in said refined raw material 1,4-butanediol-containing solution is reduced.

15. The method as claimed in claim 1, comprising step (a) and step (b).

16. The method as claimed in claim 1, comprising step (a).

17. The method as claimed in claim 1, comprising step (b).

18. The method as claimed in claim 1, wherein the concentration of a cyclic carbonyl compound having a carbon atom number of 5 or 6 in the refined 1,4-butanediol obtained in said step (d) is 10 ppm by mass or less.

19. The method as claimed in claim 1, wherein the concentration of a cyclic carbonyl compound having a carbon atom number of 5 or 6 in the refined 1,4-butanediol obtained in said step (d) is 2-6 ppm by mass.

* * * * *